United States Patent
Bryskhe et al.

(10) Patent No.: US 8,565,854 B2
(45) Date of Patent: Oct. 22, 2013

(54) METHOD AND SYSTEM FOR DIFFUSION MAGNETIC RESONANCE IMAGING

(75) Inventors: Karin Bryskhe, Åkarp (SE); Daniel Topgaard, Lund (SE); Anna Stenstam, Lund (SE)

(73) Assignee: CR Development AB, Lund (SE)

( * ) Notice: Subject to any disclaimer, the term of this patent is extended or adjusted under 35 U.S.C. 154(b) by 499 days.

(21) Appl. No.: 12/600,798

(22) PCT Filed: May 30, 2008

(86) PCT No.: PCT/SE2008/050634
§ 371 (c)(1),
(2), (4) Date: Nov. 18, 2009

(87) PCT Pub. No.: WO2008/147326
PCT Pub. Date: Dec. 4, 2008

(65) Prior Publication Data
US 2010/0152567 A1    Jun. 17, 2010

Related U.S. Application Data

(60) Provisional application No. 60/941,463, filed on Jun. 1, 2007, provisional application No. 60/972,962, filed on Sep. 17, 2007.

(30) Foreign Application Priority Data

May 31, 2007 (SE) ........................ 0701318
May 31, 2007 (SE) ........................ 0701332
Sep. 17, 2007 (SE) ........................ 0702063

(51) Int. Cl.
*A61B 5/00*    (2006.01)

(52) U.S. Cl.
USPC ........... 600/410; 324/307; 324/308; 324/309; 600/407; 436/173

(58) Field of Classification Search
USPC ................. 600/410, 411, 407; 324/307–309; 382/128; 436/173
See application file for complete search history.

(56) References Cited

U.S. PATENT DOCUMENTS 33,391 A    10/1861    Houston
6,265,872 B1    7/2001    Heid
(Continued)

FOREIGN PATENT DOCUMENTS

DE    10 2005 053 269 B3    4/2007
JP    06-000169 A    1/1994
(Continued)

OTHER PUBLICATIONS

Callaghan, "Diffusion-diffusion correlation and exchange as a signature for local order and dynamics," Journal of Chemical Physics, vol. 120, No. 8, Feb. 22, 2004, pp. 4032-4038.

(Continued)

*Primary Examiner* — Unsu Jung
*Assistant Examiner* — Amanda Lauritzen
(74) *Attorney, Agent, or Firm* — Birch, Stewart, Kolasch & Birch, LLP

(57) ABSTRACT

A method, system, computer-readable medium, use, and pulse sequence for magnetic resonance imaging or nuclear magnetic resonance is provided for determining the rate of molecular exchange between components with different diffusion characteristics. The present invention encodes the magnetic resonance signal for exchange utilizing judiciously designed protocols for varying the parameters of a pulse sequence comprising a pair of diffusion weighting blocks separated by a mixing time.

7 Claims, 11 Drawing Sheets

(56) References Cited

U.S. PATENT DOCUMENTS

| | | | |
|---|---|---|---|
| 6,614,226 B2* | 9/2003 | Wedeen | 324/309 |
| 6,842,000 B2 | 1/2005 | Norris et al. | |
| 7,355,407 B1 | 4/2008 | Zhang | |
| 2004/0071324 A1* | 4/2004 | Norris et al. | 382/128 |
| 2010/0033182 A1* | 2/2010 | Ozarslan et al. | 324/309 |
| 2010/0090694 A1* | 4/2010 | Heid et al. | 324/309 |
| 2011/0234223 A1* | 9/2011 | McColl et al. | 324/309 |

FOREIGN PATENT DOCUMENTS

| | | |
|---|---|---|
| JP | 06-054816 A | 1/1994 |
| JP | 06-114029 A | 4/1994 |
| JP | 06-121781 A | 5/1994 |
| JP | 07-079939 A | 3/1995 |
| JP | 09-173315 A | 7/1997 |
| JP | 10-248824 A | 9/1998 |
| JP | 11-267111 A | 10/1999 |
| JP | 11-285481 A | 10/1999 |
| JP | 2000/279390 A | 10/2000 |
| JP | 2002/000579 A | 1/2002 |
| JP | 2002/306450 A | 10/2002 |
| JP | 2004/526491 A | 9/2004 |

OTHER PUBLICATIONS

Alexander et al., "Elimination of Eddy Current Artifacts in Diffusion-Weighted Echo-Planar Images: The Use of Bipolar Gradients", MRM, vol. 38, 1997, pp. 1016-1021, XP000729810.

Callaghan et al., "Locally anisotropic motion in a macroscopically isotropic system: displacement correlations measured using double pulsed gradient spin-echo NMR", Magnetic Resonance in Chemistry, vol. 40, 2002, pp. S15-S19, XP007917521.

Callaghan et al., "Use of the second dimension in PGSE NMR studies of porous media", Magnetic Resonance Imaging, vol. 21, 2003, pp. 243-248, XP007917495.

Mitra, "Multiple wave-vector extensions of the NMR pulsed-field-gradient spin-echo diffusion measurement", Physical Review B, vol. 51, No. 21, Jun. 1, 1995, pp. 15074-15078, XP007917522.

Reese et al., "Reduction of Eddy-Current-Induced Distortion in Diffusion MRI Using a Twice-Refocused Spin Echo", Magnetic Resonance in Medicine, vol. 49, 2003, pp. 177-182, XP002483794.

Schachter et al., "Measurements of Restricted Diffusion Using an Oscillating Gradient Spin-Echo Sequence", Journal of Magnetic Resonance, vol. 147, 2000, pp. 232-237, XP004406771.

Sun et al., "Background gradient suppression in pulsed gradient stimulated echo measurements", Journal of Magnetic Resonance, vol. 161, 2003, pp. 168-173, XP004421017.

Assaf Y. et al: "High b-value q-space analyzed diffusion-weighted MRI: Application to multiple sclerosis", Magnetic Resonance in Medicine, Academic Press, Duluth, MN, US, vol. 47, No. 1, Jan. 1, 2002; pp. 115-126, XP007913525.

Wilm B.J. et al.: "Reduced field-of-view MRI using outer volume suppression for spinal cord diffusion imaging", Magnetic Resonance in Medicine, Academic Press, Duluth, MN, US vol. 57, No. 3, Mar. 1, 2007, pp. 625-630; XP007918911.

* cited by examiner

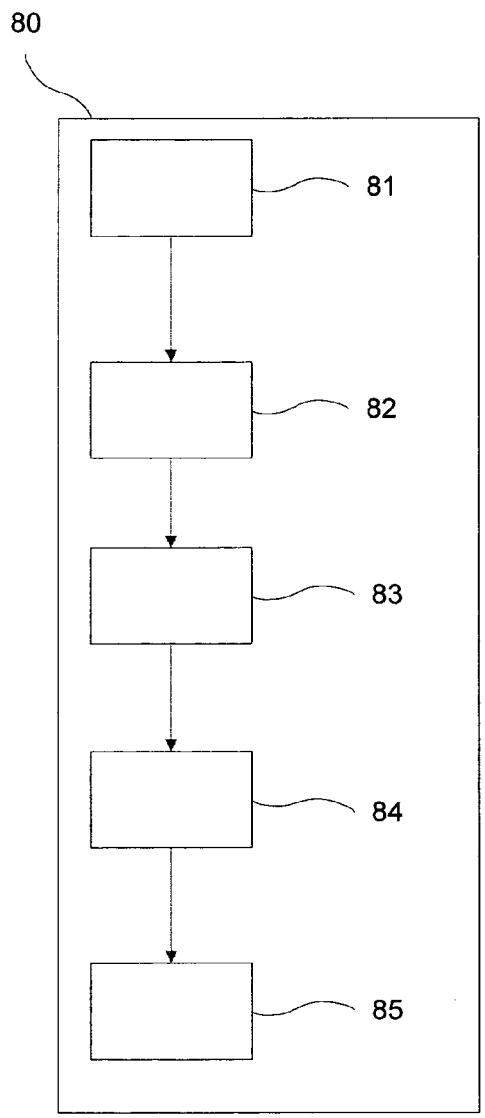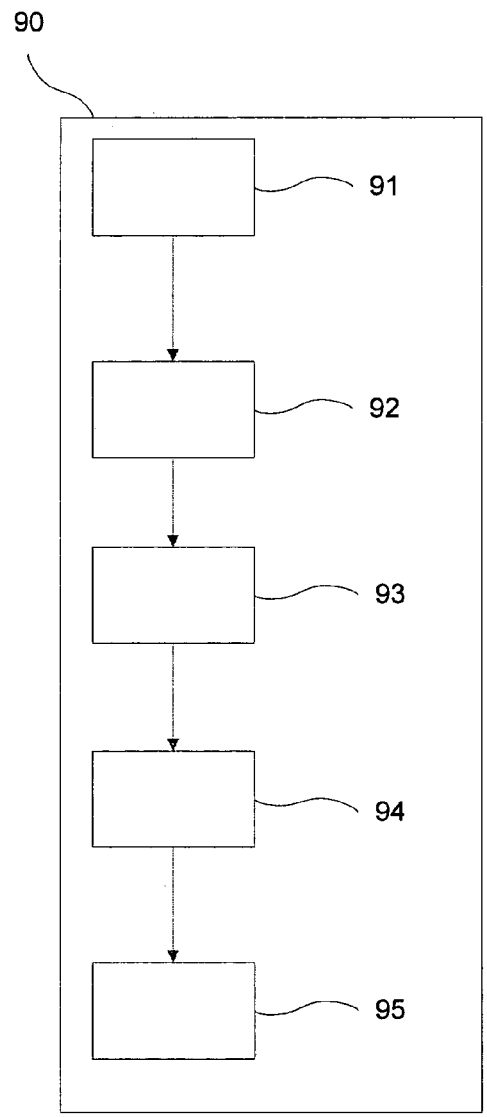
Fig. 8                    Fig. 9

METHOD AND SYSTEM FOR DIFFUSION MAGNETIC RESONANCE IMAGING

This application is the National Phase of PCT/SE2008/050634 filed on May 30, 2008, which claims priority under 35 U.S.C. 119(e) to U.S. Provisional Application No. 60/941,463filed on Jun. 1, 2007, 60/972,962 filed on Sep. 17, 2007 and under 35 U.S.C. 119(a) to Patent Application No. SE 0701318-8 filed in Sweden on May 31, 2007, SE 0701332-9 filed in Sweden on May 31, 2007 and SE 0702063-9 filed in Sweden on Sep. 17, 2007, all of which are hereby incorporated by reference into the present application.

FIELD OF THE INVENTION

This invention pertains in general to the field of Diffusion Nuclear Magnetic Resonance and Magnetic Resonance Imaging.

BACKGROUND OF THE INVENTION

Diffusion Nuclear Magnetic Resonance (NMR) has been used for over 40 years. For isotropic systems, i.e. systems which have the same characteristics in all directions, the measure of a diffusion coefficient may be interpreted in terms of aggregate size, permeability of the medium through which the molecules are moving, and binding events occurring between the diffusing species and larger molecules or the porous matrix. The most common Diffusion NMR techniques rely on pairs of magnetic field gradient pulses to label the NMR radio frequency signal for displacements occurring during the time between the pulses. Diffusion NMR techniques and methods of analysis are not only applied in vitro but also in the context of medical magnetic resonance imaging (MRI) for the detection of pathological conditions such as ischemic stroke, demyelinization disorder, and tumours.

To distinguish whether a molecule is inside or outside a closed compartment is of outmost importance for a number of studies, e.g. the controlled release of an active substance or molecular transport in tissue and biological fluids. Permeability studies are therefore performed within the pharmaceutical sciences as well as the medical and biological departments.

In both imaging and non-imaging (spectral) experiments different non-invasive means are used to receive a specific contrast. Today these are often based on the diffusion coefficients. A common way is to rely on curve fittings on a simple diffusion experiment using the Kärger model (Kärger, J., H. Pfeifer, and W. Heink. 1988. Principles and applications of self-diffusion measurements by nuclear magnetic resonance. Adv. Magn. Reson. 12:1-89). A common diffusion experiment involves a diffusion encoding block. This is sometimes used also in MRI as a means of contrast.

The publication "Diffusion-diffusion correlation and exchange as a signature for local order and dynamics" by P. T. Callaghan et al, JOURNAL OF CHEMICAL PHYSICS VOLUME 120, NUMBER 8 22 FEB. 2004 discloses two-dimensional nuclear magnetic resonance experiments in the examination of local diffusional anisotropy under conditions of global isotropy. The methods, known as diffusion-diffusion correlation spectroscopy and diffusion exchange spectroscopy, employ successive pairs of magnetic field gradient pulses, with signal analysis using two-dimensional inverse Laplace transformation. However, a drawback with the method is that the proposed method is very time consuming due to the fact that the experiment, even in its most simple protocol, has to be repeated, in practice, at least 100 times. Where the purpose is a MRI image of human the time duration for the experiment would exceed what is viable.

In summary, up until now the currently available Diffusion NMR methods for estimating permeability exchange are either very time consuming (Callaghan) or rely on curve-fitting with only weak dependence between the estimated parameters and the information in the experimental data (Kärger). Other known methods that could be used to obtain the exchange times are invasive methods, such as observations of the diffusion of a marker molecule by means of light scattering, microscopy, absorption spectroscopy and X-ray. This is not only difficult to use in vivo due to the toxicology risks but one could never assure that the tissue and body fluids are unaffected by the introduced marker.

Hence, an improved method, system, computer-readable medium, and use would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a method, system, and computer-readable medium, and use according to the appended patent claims.

According to one aspect of the invention, a method is provided. The method comprises emitting a radio frequency pulse sequence towards an object being subjected to a magnetic field, wherein said object comprises a molecule having an atom with a nuclear spin differing from 0, emitting a gradient pulse sequence towards said object, detecting a magnetic resonance signal from said object corresponding to said emitted radio frequency pulse sequence, and processing said magnetic resonance signal. Moreover, the method is characterized in that said gradient pulse sequence comprises a filter block configured to reduce at least a part of the distribution of diffusion coefficients of said object, and a diffusion encoding block occurring at a predetermined time after emitting said filter block, and said processing comprising comparing a portion of said magnetic resonance signal with a portion of a predetermined magnetic resonance signal, resulting in a compared signal, wherein the portion of said predetermined magnetic resonance signal is either user defined or resulting from a previously applied gradient pulse sequence.

According to another aspect of the present invention a system is provided. The system comprises a radio frequency pulse unit for emitting a radio frequency pulse sequence towards an object being subjected to a magnetic field, wherein said object comprises a molecule having an atom with a nuclear spin differing from 0, a gradient pulse unit for emitting a gradient pulse sequence towards said object, a detector unit for detecting a magnetic resonance signal from said object corresponding to said emitted radio frequency pulse sequence, a processing unit for processing said magnetic resonance signal, characterized in that said gradient pulse sequence comprises a filter block configured to reduce at least a part of the distribution of diffusion coefficients of said object, and a diffusion encoding block occurring at a predetermined time after emitting said filter block, and said processor unit is configured to compare a portion of said magnetic resonance signal with a portion of a predetermined magnetic resonance signal, resulting in a compared signal, wherein said portion of said predetermined magnetic resonance signal is either user defined or resulting from a previously applied gradient pulse sequence.

According to yet another aspect of the invention a computer-readable medium for magnetic resonance imaging having embodied thereon a computer program for processing by a computer is provided. The computer program comprises a radio frequency pulse code segment for emitting a radio frequency pulse sequence towards an object being subjected to a magnetic field, wherein said object comprises a molecule having an atom with a nuclear spin differing from 0, a gradient pulse code segment for emitting a gradient pulse sequence towards said object, a detector code segment for detecting a magnetic resonance signal from said object corresponding to said emitted radio frequency pulse sequence, a processing code segment for processing said magnetic resonance signal, characterized in that said gradient pulse sequence comprises a filter block configured to reduce at least a part of the distribution of diffusion coefficients of said object, and a diffusion encoding block occurring at a predetermined time after emitting said filter block, and said processor code segment (95) is configured to compare a segment of said magnetic resonance signal with a portion of a predetermined magnetic resonance signal, resulting in a compared signal, wherein said portion of said predetermined magnetic resonance signal is either user defined or resulting from a previously applied gradient pulse sequence.

According to another aspect of the invention a medical workstation comprising means for performing the method is provided.

According to an aspect of the invention a use of the method as a diagnostic tool for diagnosing a disease or disorder is provided.

According to an aspect of the invention a use of the method for studying the metabolism of living cells in vivo is provided.

According to an aspect of the invention a use of the method for studying the transmembrane diffusion of a medical drug through the cell membranes is provided.

According to another aspect of the invention a pulse sequence for use in a Magnetic Resonance Imaging system is provided. The pulse sequence comprises a filter block configured to reduce at least a part of the distribution of diffusion coefficients of an object being subjected to a magnetic field, wherein said object comprises a molecule having an atom with a nuclear spin differing from 0, and a diffusion encoding block occurring at a predetermined time after emitting said filter block.

The general solution according to the invention is that it utilizes a sequence of gradient pulses as a filter on a diffusion experiment. Thereby identical molecules can be analyzed separately and differentiated based on how restricted their diffusion is. The exchange time, i.e. the time it takes for a molecule to diffuse out of the confined compartment, and vice versa, is an important parameter that is obtainable utilizing the present invention according to some embodiments. The exchange time is a measure of the permeability of the barrier for the specified molecule.

The present invention according to some embodiments offers a new contrast mode for MRI in systems where the studied molecule is not diffusing in the same way throughout the sample, i.e. where the exchange times between intra- and extra cellular compartments are different.

Another advantage with the present invention according to some embodiments is that the overall experiment time duration needed is significantly reduced by magnitudes as compared to prior art solutions.

The shorter overall experiment time duration enables the present invention according to some embodiments to be used in vivo, e.g. such as a means for contrast in Magnetic Resonance Imaging (MRI). Current diffusion MRI images do only indirectly contain information regarding exchange times as an artefact, difficult to quantify and thereby relate to pathological conditions.

The present invention according to some embodiments may be utilized to create an image visualizing the exchange times of an investigated sample e.g. such as colour gradients.

The present invention may according to some embodiments be used as a diagnostic tool for a variety of diseases or disorders such as infarct, stroke and tumours since the exchange times are a measure of cell permeability.

Furthermore, the invention according to some embodiments provides for a non-invasive technique to study the metabolism of living cells in vivo, e.g. the presence and fraction of extra- and intracellular glucose with changes in the environment or membrane composition.

Moreover, the present invention according to some embodiments does not need background information from other experiments, such as the shape or diffusion coefficient of the studied molecule, in order to obtain a reliable exchange time result. Information regarding the shape of the studied molecule is not needed to extract the exchange time. The diffusion coefficient is itself a result of the first part of the experiment, the normal diffusion NMR experiment.

Moreover, as the present invention according to some embodiments is based on the combination of a filter block and a diffusion encoding block it provides advantages as compared to current techniques.

Compared to a common diffusion encoding MRI experiment the present invention according to some embodiments may result in an image where the contrast is dependent on differences in exchange time (see FIG. 6). The contrast mode obtained by the present invention may be combined with already existing contrast modes. Current MR images do only indirectly contain this information as an artefact, where the information about exchange times is non extractable.

The method according to some embodiments and the method by Callaghan et al. could be described as diffusion experiments performed at different times.

Compared to known Diffusion-diffusion correlation spectroscopy and diffusion exchange spectroscopy by Callaghan et al., the present invention according to some embodiments may give the same result (the exchange time) in a much shorter time. Due to the shorter experiment duration time the present invention according to some embodiments opens up for the possibility to study the exchange time in biological samples, e.g. human patients, in vivo. This has not been possible until now.

The reason why the experiment time is decreased by magnitudes is due to the filter block according to some embodiments. By using a filter block the number of experiments necessary to obtain the information is decreased. The method by Callaghan et al. for example uses 16 times 16 experiments since the two diffusion encoding blocks have to vary independently as required by the subsequent two-dimensional inverse Laplace transform. The present invention according to some embodiments involves only 1 times 16 experiments, since the incremented first diffusion encoding block in the method of Callaghan is replaced by a filter block having a fixed b-value (explained more in detail below). The fixed b-value of the diffusion filter block is set according to some embodiments so that the fast diffusing component in the resulting image is masked.

With a judiciously chosen filter block and mixing time, the present invention, according to some embodiments, yields images with contrast based on molecule exchange over the cell membrane. This image could be recorded in the same amount of time as commonly used high b-value q-space images (Cohen Y, Assaf Y (2002) High b-value q-space analyzed diffusion-weighted MRS and MRI in neuronal tissues—a technical review. *NMR Biomed.* 15, 516-542).

BRIEF DESCRIPTION OF FIG. 1-9

These and other aspects, features and advantages of which the invention is capable of will be apparent and elucidated from the following description of embodiments of the present invention, reference being made to the accompanying drawings, in which FIG. 1 is an illustration showing a commonly known standard pulse sequence for diffusion NMR/MRI;

FIG. 8 is an illustration showing a system according to an embodiment;

FIG. 9 is an illustration showing a computer-readable medium according to an embodiment;

The explanations of other figures, FIGS. 10 to 21, are given further below in the description.

DESCRIPTION OF SOME EMBODIMENTS OF THE PRESENT INVENTION

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Figure 1:
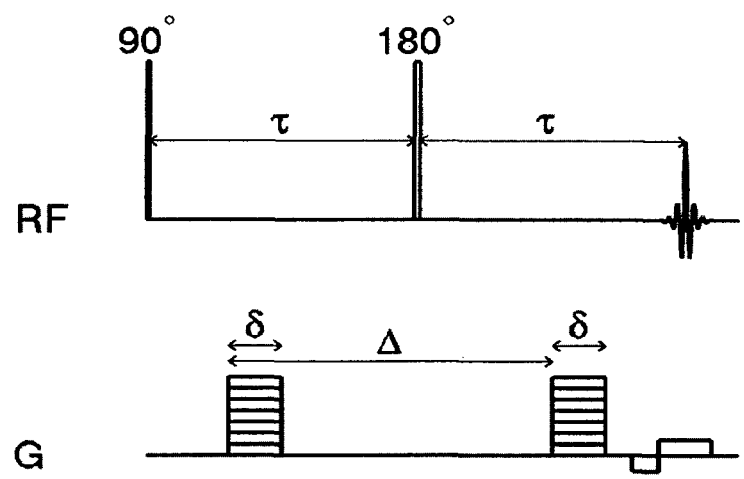

FIG. 1 illustrates a commonly known standard pulse sequence for diffusion NMR/MRI. The signal is labelled for diffusion using two gradient pulses of duration δ and strength G. Δ is the time between the onset of the pulses. The signal intensity I is decaying according to $I=I_0 e^{(-bD)}$ where $b=(\gamma G\delta)^2(\Delta-\delta/3)$, D is the self-diffusion coefficient, and $I_0$ is the signal intensity at zero gradient strength. The signal is recorded as a function of G throughout the experiment.

Figure 2:
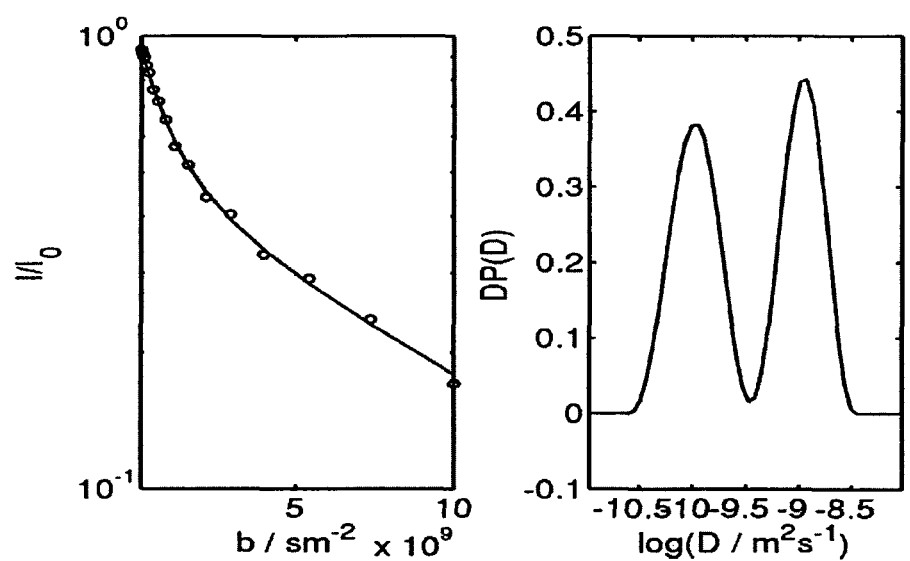
FIG. 2 is an illustration showing commonly known simulated signal decay $I/I_0$ as a function of b for a system with equal amounts of two diffusion components.

FIG. 2 illustrates a commonly known simulated signal decay $I/I_0$ as a function of b for a system with equal amounts of two diffusion components having the diffusion coefficients $10^{-9}$ and $10^{-10}$ $m^2 s^{-1}$. Using commonly known de-convolution of the decay curve using an inverse Laplace transform algorithm yields the distribution of diffusion coefficients DP(D) from which the amount of the various diffusion components may be estimated.

The following description focuses on embodiments of the present invention applicable to Diffusion NMR/MRI.

A general solution according to the invention is that it utilizes a sequence of gradient pulses as a filter on a diffusion experiment. Thereby identical molecules may be analyzed separately and differentiated based on how restricted their diffusion is. The studied molecule has the same local diffusion coefficient whether it is inside or outside the compartment. However, the presence of barriers results in a diffusion coefficient spectrum with at least two apparent diffusion coefficients. As an example consider a sample of intra- and extra cellular water molecules. Molecules located in the continuous water phase outside cells are only marginally affected by the presence of the cells, and their diffusion coefficient is similar to the bulk value ($2.3*10^{-9}$ $m^2/s$ at room temperature). The motion of molecules located within the cells is hindered by the presence of the cellular membranes and the apparent diffusion coefficient measured by NMR is substantially reduced from the bulk value. For many cellular systems this reduction could be several orders of magnitude. These two diffusion coefficients may be denoted slow and fast diffusion. The exchange time, i.e. the time it takes for a molecule to diffuse out of the confined compartment, such as a cell membrane, to the external surrounding, and vice versa, is an important parameter that is obtainable utilizing the present invention according to some embodiments. The exchange time is a measure of the permeability of the barrier for the specified molecule.

In simplification a general idea of the invention is to perform a normal diffusion experiment, however utilizing a pulse sequence having at least two parts, wherein the first part of the pulse sequence is used as a filter for the remaining measurement, and the second part may be a commonly known pulse sequence referred to as diffusion encoding block throughout this specification, see FIG. 1.

Throughout this specification the relation between the first diffusion component and second diffusion component is that the second diffusion component, the faster component, has a larger diffusion coefficient than the first, slower, diffusion component. For simplicity the terms "slow" and "fast" are used, however these terms only indicate that the slow component has lower apparent diffusion coefficient than the fast, and conversely.

Figure 3:
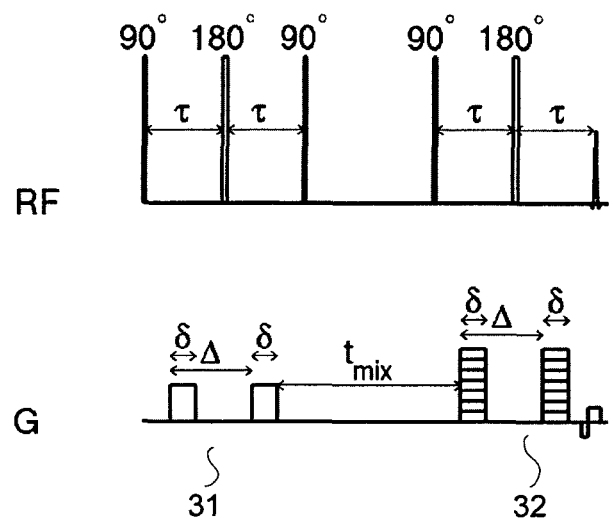
FIG. 3 is an illustration showing an embodiment.
Figure 4:
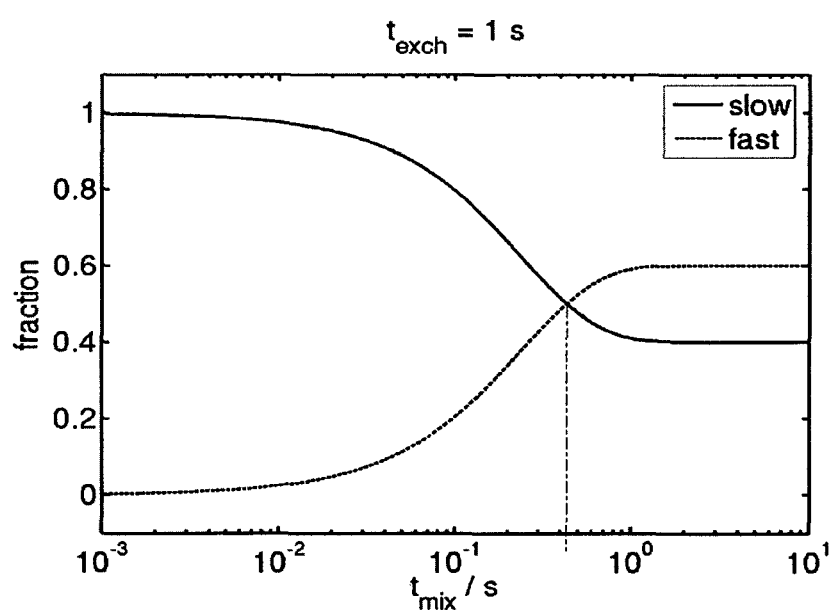
FIG. 4 is an illustration showing an embodiment.

In an embodiment of the present invention, according to FIG. 3, a pulse sequence is provided. The pulse sequence may e.g. be used to separately analyze identical molecules and differentiate the molecules based on how restricted their diffusion is in a Diffusion NMR/MRI system. The pulse sequence comprises a filter block 31, comprising a first pulse sequence, being configured to filter away or mask the signal originating from fast diffusion components in an investigated sample, such as a human, while retaining the signal from slow diffusion components of said sample. Accordingly, only the signal decay of the slower diffusion component (inside a compartment) is stored by use of a RF pulse during the mixing time to protect it from $T_2$ relaxation by storage in for example the z-direction. The pulse sequence further comprises a diffusion encoding block 32, comprising a second pulse pair, being configured to act in the same way as a standard diffusion NMR/MRI experiment. After each diffusion encoding block a Magnetic Resonance image signal may be recorded according to commonly known procedures. A series of measurements, with varying diffusion encoding and consequently b-value, results in a series of images which may be subjected to inverse Laplace transform for providing the distribution of diffusion coefficients and the amplitudes of the slow and fast components. With increasing mixing time the signal from the faster component will reappear if there is an exchange between inside and outside, in practice, on the time scale in the order of 0.1-1000 ms. In order to accurately estimate the time for exchange, one may have to acquire a series of images, i.e. a series of measurements, such as at least ten in a practical implementation, for varying mixing times and consequently different fractions of fast and slow diffusion components (FIG. 4). This means that, according to some embodiments, that at least two series of measurements with varying mixing time $t_{mix}$ are performed, each containing a filter block and subsequent diffusion encoding block with a series of b-values.

By definition, and as is commonly known for the skilled artisan, each diffusion encoding block provides diffusion contrast for the resulting Magnetic Resonance image signal. This means that without a diffusion encoding block the resulting image signal is not encoded for diffusion.

Accordingly, after each diffusion encoding block a resulting Magnetic Resonance image signal may be recorded. Hence, by performing two consecutive series of measurements, with varying mixing time, a first image signal corresponding to the first series of measurements and a second image signal corresponding to the second series of measurements is acquired. As mentioned above the resulting series of images may be subjected to inverse Laplace transform for providing the distribution of diffusion coefficients, and from which the slow and fast components may be estimated. The difference in the fast diffusion component between the two series of images apparently is a measure of the exchange time. A value of the exchange time may be calculated, based on commonly known algorithms, by comparing the amplitudes of the fast and slow components for the two series of images.

Consequently, the exchange time of the fast and slow diffusion components occurring during the mixing time $t_{mix}$ may be retrieved. Accordingly, the pulse sequence according to some embodiments makes it possible to analyze the reappearance of the fast diffusion component in the signal after filtration as a function of time. This gives the desired parameter, the exchange time between components with restricted and free diffusion, and the ratio between the two signals may be correlated to the ratio between the number of molecules with free respectively restricted diffusion.

In some embodiments the magnetic field gradients in the filter block and the diffusion block have substantially the same direction. For example, this means that if the filter block is oriented in the x-direction, also the diffusion encoding block is oriented in the x-direction or substantially in the x-direction. By substantially is meant that direction between the filter block and diffusion encoding block may differ slightly without too adversely affecting the result regarding exchange.

Consider a sample with one free and one restricted component characterized with the diffusion coefficients $D_{fast}$ and $D_{slow}$ respectively. $P_{fast}$ is the fraction of fast molecules in the sample. The normalized diffusion NMR signal E measured with a standard Stejskal and Tanner experiment may be approximated as:

$$E(b)=(1-P_{fast})e^{-b \cdot Dslow}+P_{fast} \cdot e^{-b \cdot Dfast}$$

where b is the diffusion sensitizing parameter defined below. The diffusion sensitizing parameter b describes the degree of diffusion weighting or diffusion sensitization, meaning the application of a sequence of strong gradients to elicit differences in the diffusivity of water molecules within a sample.

For the Stejskal-Tanner experiment involving a pulsed pair of approximately rectangular gradients around a 180° radiofrequency pulse that is most commonly implemented on clinical MR scanners—the b value is determined by the duration (δ) and strength (G) of the sensitizing pulsed gradients, and the time interval between the two pulsed gradients (Δ) is determined according to the equation:

$$b=\gamma^2 G^2 \delta^2 (\Delta-\delta/3)$$

where γ is the gyromagnetic ratio. Thus, the b value (diffusion sensitization) can be increased by using stronger (G) and longer (δ) pulsed gradients or by lengthening the time between the pulsed gradients (Δ).

In some embodiments, in the limit $D_{fast} \gg D_{slow}$, the value of b may be adjusted to completely remove or mask the signal from the free (fast) component while completely preserving the signal from the slow component. In some embodiments for an ideal experiment the b value of the filter block is fixed within the following limits: $1/D_{fast} \ll b \ll 1/D_{slow}$. This definition of the b-value is for the ideal theoretical case however, in practice, the limits are in the same order of magnitude. With a correct choice of b-value for the filter block the fast component is masked.

In the diffusion encoding block the b value is varied within the limits $0.1/D_{fast} < b < 5/D_{slow}$. (Callaghan et al. use two sets of diffusion encoding blocks and thus they are varying the b-values independently in both blocks resulting in a two-dimensional data matrix with typically 16×16 entries).

With appropriately applied radio frequency (RF) pulses including the filter block of the pulse sequence according to some embodiments, this signal only comprising the slow component may be stored in e.g. the z-direction and recalled after a mixing time $t_{mix}$.

By providing the diffusion encoding block of the pulse sequence according to some embodiments, after the signal has been recalled a total signal similar to the equation for E(b) according to above will be obtained. The difference compared to prior art solutions will however be that the amplitudes of the various diffusion components depend on the presence of exchange. With no exchange between the compartments, the apparent slow fraction $P_{slow}'$ equals 1—all signal comes from the restricted component. For long $t_{mix}$, $P_{slow}'$ is approaching the true slow fraction, $P_{slow}$. The residence time for the molecules in the restricted compartment may be estimated by measuring $P_{slow}'$ was a function of $t_{mix}$.

In some embodiments, the condition for all diffusion blocks, the filter block as well as the diffusion encoding block, is the same. In order for a spin echo to form, the integral of the gradient over time must equal zero (ref. Hahn, E. L. *Phys. Rev.* 1950, 80, 580)

$$\int_{t_0}^{t_1} g(t)\,dt = 0.$$

Thus the shape, magnitude, number and sign of the gradient pulses and combination of gradient and RF pulses may be various as long as the integral is zero. A second condition concerns the b value that is defined according to:

$$b = \gamma^2 \int_0^t \left( \int_0^{t'} g(t'')\,dt'' \right)^2 dt'$$

In the filter block the b value according to some embodiments is fixed throughout the experiment while it is varied in the diffusion encoding block throughout the experiment. The fact that it is fixed and not varied in the first block (called Filter block throughout this specification) is new and crucial for the reduction in experimental time compared with commonly known methods. To make sure that the fast component is filtered away one may analyze the diffusion experiment with an inverse Laplace Transformation. This results in a distribution of diffusion coefficients where the fast component is absent. This may be performed by letting the mixing time for a single series of measurements be close to zero, i.e. that the filter block is directly followed by the diffusion encoding block. The resulting series of image signals will then comprise information regarding the efficacy of the filter block, i.e. how well the fast diffusion components are masked away. This provides a way for confirming that the designed filter block achieves the desired purpose of masking away the fast diffusion component.

In an embodiment, according to FIG. 4, the simulated evolution of the fractions or ratio of second (fast) and first (slow) diffusion components as a function of mixing time $t_{mix}$ for a sample with 60% of the second fraction at equilibrium and an exchange time constant $t_{exch}=1$ s is provided. As may be observed from FIG. 4, momentarily after introduction of the filter block comprised in the pulse sequence according to some embodiments, there will be almost zero percentage of the fast component, and consequently almost 100% of the signal will originate from the slow diffusion component. As time passes the fast component will increase provided that there is trans-compartment diffusion within the sample. Accordingly, the percentage of the slow diffusion component will decrease as a function of time. By the time between $10^{-0,6}$ and $10^{-0,5}$ the fractions of the two components will be equal and after approximately the time $t_{exch}=1$ s equilibrium will occur and there will be a 60% fraction of the second (fast) diffusion components. Accordingly, each combination of filter block and diffusion encoding block according to some embodiments will result in information regarding the fraction between the investigated diffusion components at the chosen $t_{mix}$.

In some embodiments the full experiment, i.e. total pulse sequence, comprises the filter block masking the fast diffusion component in the received signal, and at least one diffusion encoding block. The diffusion encoding block gives information about the fraction of fast and slow diffusion components after a certain $t_{mix}$ time in relation to the fraction resulting by introduction of the filter block. In this way the recall behaviour of the fast component in the sample, and accordingly the exchange time, may be studied in detail. Subsequent diffusion blocks might contain other valuable information. In this manner the combination of filter block and diffusion encoding blocks according to some embodiments may comprise at least two blocks where at least one is a filter block.

Figure 5:
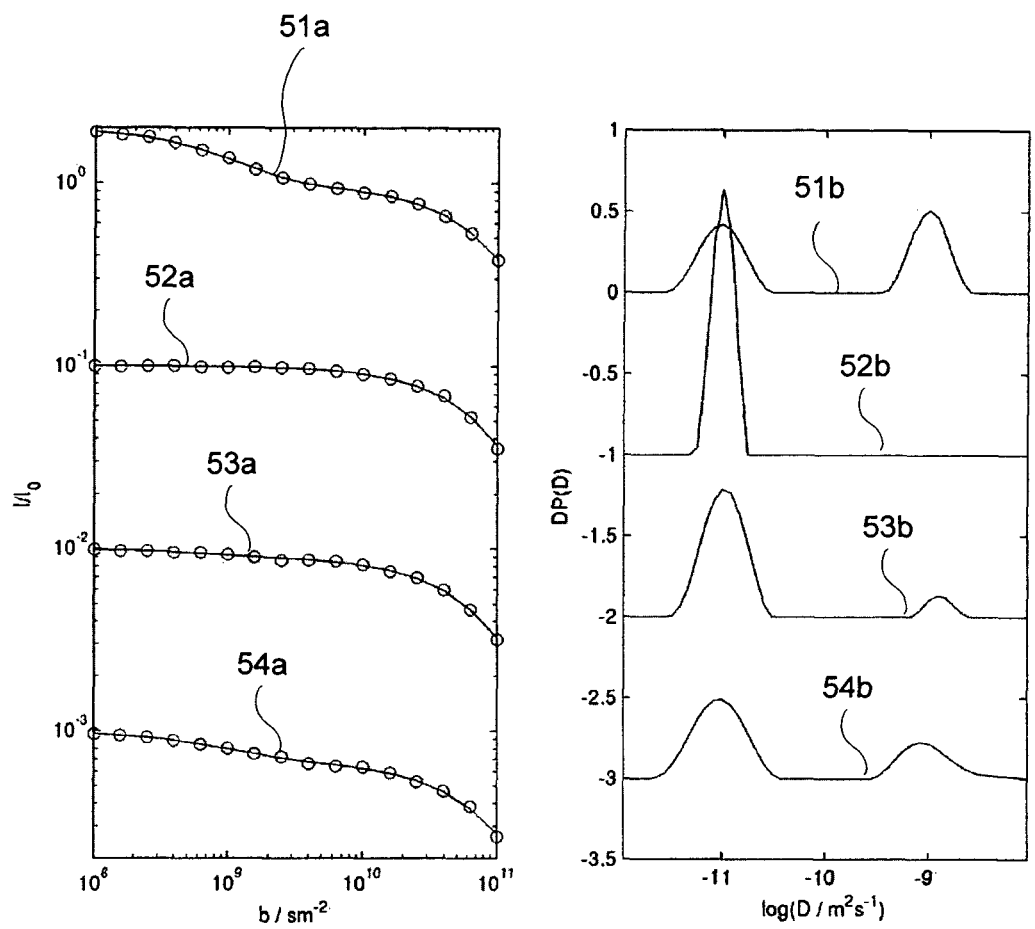
FIG. 5 is an illustration showing different signal intensity decays versus the diffusion sensitizing parameter b, and the corresponding distributions of diffusion coefficients according to an embodiment.

FIG. 5 illustrates different signal intensity decays versus the diffusion sensitizing parameter b, and the corresponding distributions of diffusion coefficients as obtained by commonly known Inverse Laplace Transforms (ILT). The signal decay 51a from two fractions of free (fast) and restricted (slow) diffusion and its corresponding diffusion coefficients 51b are shown based on a commonly known diffusion experiment. The signal decay 52a is filtered by means of a first measurement comprising a filter block and a diffusion encoding block according to some embodiments wherein the mixing time is close to zero. As may be clearly observed the corresponding distribution of diffusion coefficients 52b, show that the fast diffusion component has been masked. Signal decay 53a results from a second series of measurements wherein the mixing time between the filter block and the diffusion encoding block in the second series of measurements is larger than the mixing time for the first series of measurements. The corresponding distribution of diffusion coefficients 53b show that the fast diffusion component has reappeared. Performing a third series of measurements having a mixing time larger than the mixing time for the second series of measurements will result in a signal decay 54a with its corresponding distribution of diffusion coefficients 54b. As may be observed the fast diffusion component is still increasing as compared to distribution of diffusion coefficients 53b. FIG. 5 shows the reappearance of the signal from the fast component as a function of time, and also a way to implement the present invention according to some embodiments. This feature provides a great advantage over commonly known techniques, i.e. studying the reappearance and exchange time between different diffusion components within a sample, due to that it is order of magnitude faster. The time for a signal to reappear equals the exchange time between free and restricted diffusion for the studied molecule. The time is a measure of the permeability of the barrier for the specified molecule within the sample. This information is difficult to obtain by other methods on a reasonable time scale for practical purposes. Current techniques are so slow that they may not be used in e.g. MRI applications in vivo due the situation of the patient as well as the health economy. It is not reasonable to believe that it would be feasible to perform such an examination on a regularly basis since it could take several hours or more.

The embodiments of the invention are not limited to the exemplified diffusion coefficients, which merely depend on which kind of material that is analyzed. For instance, the diffusion coefficients differs between water molecules in liquid, gas molecules, and more viscous materials such as e.g. glycerol. The method according to some embodiments may be used to detect exchange regardless of the material in the investigated sample.

In some embodiments, an estimate of the exchange time may be given with only one measurement, i.e. using one filter block and one encoding block. This may be performed by the knowledge that the utilized filter block masks the fast diffusion component in a predetermined degree, such as that it completely masks away the fast diffusion component. In addition, the true fraction of fast or slow component in the sample needs to be known, see FIG. 4. The resulting image signal comprising information regarding the reappearance, due to the mixing time $t_{mix1}>0$, of the fast component may then be compared to the predetermined degree of the fast component due to the filter block at time zero. For example, if it is known that the filter block completely removes the fast diffusion component, the fast diffusion components in the resulting image signal, enabled due to the encoding block, will hence comprise the same information as the comparison between a first image signal resulting from a first measurement comprising a filter block and an encoding block with zero mixing time, and a second image signal resulting from a second measurement comprising a filter block and an encoding block having the same mixing time $t_{mix1}>0$. Accordingly, a value of the exchange time may be estimated with only one measurement based on a user definition, such as an assumption or knowledge of the impact of the used filter block. Accordingly, in some embodiments a predetermined image signal corresponding to the assumption or knowledge of the user, may be user defined. This predetermined image signal may thus be used during comparison with the signal resulting from a real measurement comprising a filter block and an encoding block according to some embodiments.

A previously recorded image signal resulting a previously applied filter block and encoding block according to some embodiments may also be used during comparison with the recorded image signal for a current measurement in order to calculate the exchange time.

Figure 6:
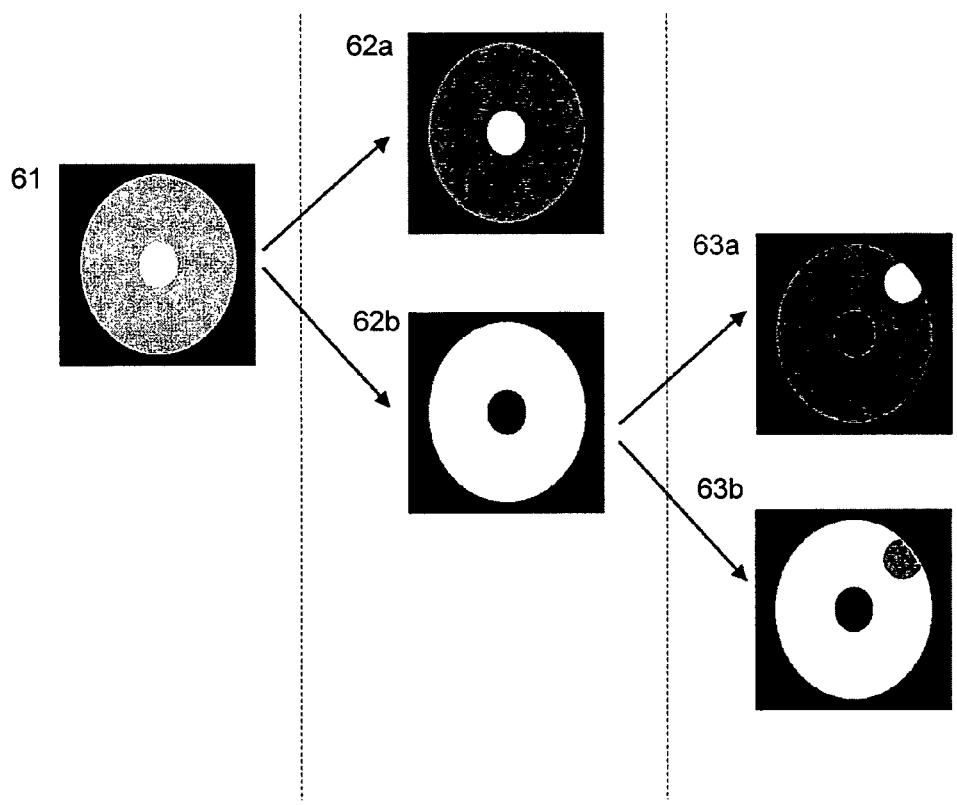
FIG. 6 is an illustration showing a comparison between the image results of an analyzed sample obtainable through prior art NMR/MRI protocols and the results obtained through the pulse sequence according to an embodiment.

FIG. 6 illustrates a comparison between the image results of an analyzed sample obtainable through prior art NMR/MRI protocols and the results obtained through the pulse sequence according to some embodiments. The investigated sample consists of a first and a second diffusion component, such as a fast and a slow diffusion component, respectively, having the diffusion coefficients $10^{-9}$ and $10^{-10}$ $m^2s^{-1}$, respectively, which are previously known through conventional diffusion MRI measurements using e.g. inverse Laplace transforms.

The concentrations of the two components and exchange times vary with the location within the sample. The results for a standard MRI protocol with no applied contrast are indicated in image 61. The image intensity is given by the total concentration of the two components.

The results for a commonly known diffusion MRI protocol with separation of the first and second components using inverse Laplace transform approach or a biexponential fit are indicated in image 62a (fast diffusion component), and image 62b (slow diffusion component).

The results by utilizing the pulse sequence according to some embodiments of the present invention in a diffusion NMR/MRI experiment are indicated in image 63a and image 63b. Image 63a illustrates the amplitudes of the first diffusion component after application of the filter block of the pulse sequence and subsequent mixing time $t_{mix}$. Image 63b illustrates the amplitudes of the second diffusion component after application of the filter block of the pulse sequence and subsequent mixing time $t_{mix}$. The bright area in image 63b corresponds to a region where there are molecules having a wide range of diffusion coefficients and significant exchange between the first and second components during the mixing time.

Figure 7:
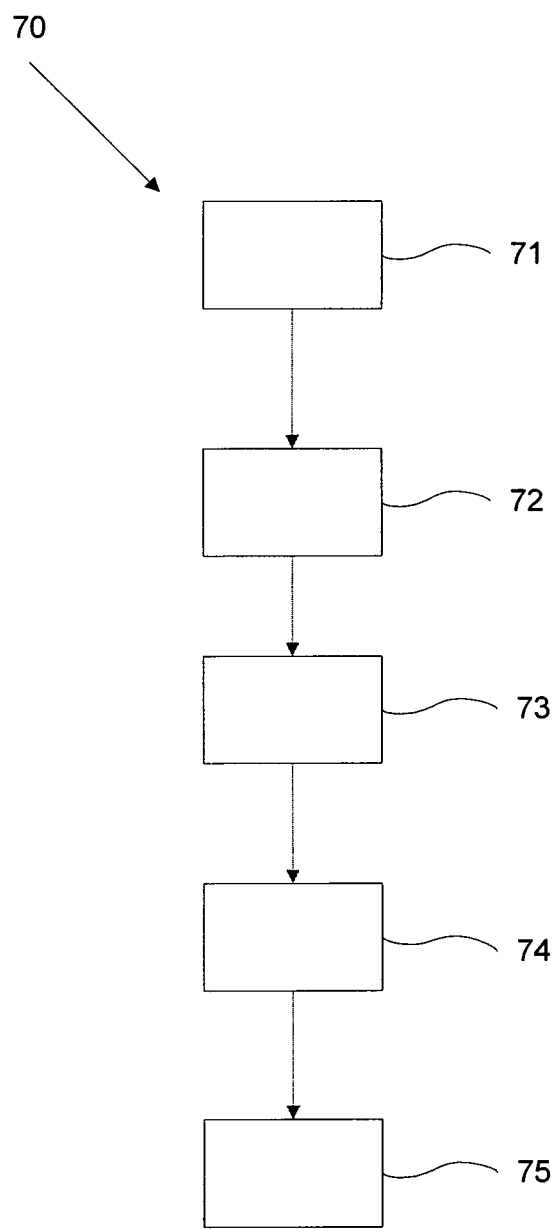
FIG. 7 is a flowchart showing a method according to an embodiment.

In an embodiment, according to FIG. 7, a method 70 for magnetic resonance spectroscopy is provided. The method comprises:
emitting 71a radio frequency pulse sequence towards an object being subjected to a magnetic field, wherein said object comprises a molecule having an atom with a nuclear spin differing from 0,
emitting 72a gradient pulse sequence towards said object,
detecting 73a magnetic resonance signal from said object corresponding to said emitted radio frequency pulse sequence,
processing 74 said magnetic resonance signal, characterized in that said gradient pulse sequence comprises a filter block configured to reduce at least a part of the distribution of diffusion coefficients of said object, and a diffusion encoding block occurring at a predetermined time after emitting said filter block,
said processing 74 comprising comparing a portion of said magnetic resonance signal with a portion of a predetermined magnetic resonance signal, resulting in a compared signal, wherein said portion of said predetermined magnetic resonance signal is either user defined or resulting from a previously applied gradient pulse sequence.

In an embodiment the method further comprises creating 75 an image based on said compared signal.

According to some embodiments the b-value is chosen so that the Diffusion encoding becomes a filter, i.e. that the signal from the fast component is substantially removed.

Related Experiments
One Set of Experiments

In one embodiment, distilled water and ordinary bakers yeast (*S. cereveciae*) was used. A solution of yeast and water, with the ratio of 1:1 (w/w), was left to sediment for 6 hours at 8° C. Subsequently; a portion of the dense solution was carefully transferred into a 5 mm Shigemi NMR tube (Sigma Aldrich), using a Pasteur pipette. A Bruker DMX-200 MHz NMR spectrometer was used to perform the measurements. The probe used was a diffusion probe with a 5 mm RF coil. The maximum gradient strength was 9.63 T and the temperature control unit of the probe had the accuracy of 0.5° C.

Diffusion experiments were performed with the use of a spin echo diffusion pulse program. A pulse sequence according to some embodiments with constant gradient amplitude in the first diffusion sequence was used. A set of experiments was carried out for few temperatures (5, 15, 20, 25, 30 and 35° C.). Each sequence was begun with a diffusion experiment for a given temperature, in order to determine the strength of the first gradient that was required to remove the signal from the fast moving water. When that was decided, the constant gradient was set and a series of experiments was carried out. For each experiment, the mixing time was increased in order to determine the speed with which the water molecules escaped the yeast cells. After the acquisition parameters were set for a series of experiments the mixing time was the only one to be changed. All the other parameters were kept constant to ensure the comparability of the experiments. Also—the parameters were kept constant throughout the different series of experiments, to make the obtained data more comparable.

The diffusion experiments, carried out in the beginning of each series of measurements, showed the existence of two diffusion coefficients in the system. As expected, the water molecules were divided into two groups: the ones that were in between the cells and those that were entrapped within the cells. The diffusion of the fast moving fraction of water molecules can be fitted with an exponential function, but the slow moving fraction diffusion cannot as expected for restricted diffusion in a pore.

Following the diffusion experiment, the above pulse series provided the results enabling to follow the changes in the system. More precisely, the growth of the fast moving fraction as the mixing time of the experiments increased.

Inverse Laplace Transform was performed using the CONTIN algorithm (Provencher, S. W., A constrained regularization method for inverting data represented by linear algebraic or integral equations; Computer Physics Communications 27:213-227 (1982)) in order to access the diffusion of slow and fast moving water molecules at different stages of the experiments.

The resulting graphs confirmed the conclusions that the fast moving water signal is increasing in its intensity. Consequentially, the slow moving water signal diminished.

The method according to some embodiments may be used in conjunction with commonly known invasive techniques where the investigated sample is doped with a contrast fluid. This could be interesting in conjunction with other methods where it is important to know the permeability of the contrast fluid used. The marker could also be of the type where the molecule of interest is doped with NMR active isotopes to make it easier to isolate the signal from the molecule of interest.

In an embodiment the method is used as a diagnostic tool in order to diagnose a disease or disorder e.g. in a human subject.

In an embodiment the method further comprises creating an image of the sample comprising a colour gradient coding the exchange times in different parts of the investigated sample. Any known colour coding procedure may be used. An advantage of this embodiment is that the colour-coded image could be used as a diagnostic tool for diagnosing a disease or disorder in e.g. a human subject.

In some embodiments the disease may be cancer and the investigated sample may comprise of benignant tissue or malignant cancer tissue. It is reasonable to believe that the rigidity of the cell membrane is altered in cancerous tissue and that this could affect the transmembrane diffusion of molecules. The present invention has been tested on healthy breast cells and cancerous breast cells. Preliminary results show a different exchange time for water. The exchange time of water is shorter for the healthy cells compared to the cancerous cells. As the cell activity is higher in cancerous tissue, this could also possibly affect the transmembrane diffusion of other cellular molecules.

In some embodiments the method may be used to monitor a medical treatment of human subject by monitoring the transmembrane diffusion of an introduced medical drug through the cell membranes.

In some embodiments the method may be used to monitor the effect of a drug on the permeability through the cell membrane of other molecules such as, water, glucose or naturally occurring peptides.

In some embodiments the method may be used for analytical purposes in vitro where there is an interest of knowing whether the diffusion of a molecule is restricted by a boundary and if so to what extent it is restricted, i.e. on which time scale it is restricted. The method according to some embodiments has been tested to study the permeability of water molecules through yeast cell membranes as a function of temperature. The result is displayed in the following table:

| Temperature (° C.) | Exchange time (s) |
| --- | --- |
| 5 | 24 |
| 15 | 8.7 |
| 20 | 4.8 |
| 25 | 1.0 |
| 30 | 0.70 |
| 35 | 0.47 |

The obtained results prove that the exchange between the molecules inside and outside the cells actually occurs. In addition it is shown that the exchange time have non-linear temperature dependence. The exchange time depends heavily on temperature. This is of interest for work with the aim of using cells as vehicles for smaller molecules.

In an embodiment, according to FIG. 8, a system for magnetic resonance imaging is provided. The system comprises a radio frequency pulse unit 81 for emitting a radio frequency pulse sequence towards an object being subjected to a magnetic field, wherein said object comprises a molecule having an atom with a nuclear spin differing from 0, a gradient pulse unit 82 for emitting a gradient pulse sequence towards said object,
a detector unit 83 for detecting a magnetic resonance signal from said object corresponding to said emitted radio frequency pulse sequence,
a processing unit 84 for processing said magnetic resonance signal, characterized in that said
gradient pulse sequence comprises a filter block configured to reduce at least a part of the distribution of diffusion coefficients of said object, and a diffusion encoding block occurring at a predetermined time after emitting said filter block, and
said processor unit 84 is configured to compare a portion of said magnetic resonance signal with a portion of a predetermined magnetic resonance signal, resulting in a compared signal, wherein said portion of said predetermined magnetic resonance signal is either user defined or resulting from a previously applied gradient pulse sequence.

In an embodiment the system further comprises an image creation unit 85 configured to create an image based on said compared signal. The image creating unit may be any known unit for creating an image based on a magnetic resonance signal.

In an embodiment the system comprises units for performing the method according to some embodiments.

In an embodiment, according to FIG. 9, a computer-readable medium having embodied thereon a computer program for processing by a processor is provided. The computer program comprises
a radio frequency pulse code segment 91 for emitting a radio frequency pulse sequence towards an object being subjected to a magnetic field, wherein said object comprises a molecule having an atom with a nuclear spin differing from 0,
a gradient pulse code segment 92 for emitting a gradient pulse sequence towards said object,
a detector code segment 93 for detecting a magnetic resonance signal from said object corresponding to said emitted radio frequency pulse sequence, a processing code segment 94 for processing said magnetic resonance signal, characterized in that said
gradient pulse sequence comprises a filter block configured to reduce at least a part of the distribution of diffusion coefficients of said object, and a diffusion encoding block occurring at a predetermined time after emitting said filter block, and
said processor code segment 95 is configured to compare a portion of said magnetic resonance signal with a portion of a predetermined magnetic resonance signal, resulting in a compared signal, wherein said portion of said predetermined magnetic resonance signal is either user defined or resulting from a previously applied gradient pulse sequence.

In an embodiment the computer program further comprises an image creation code segment 95 configured to create an image based on said compared signal.

In an embodiment the computer-readable medium comprises code segments arranged, when run by an apparatus having computer-processing properties, for performing all of the method steps defined in some embodiments.

In an embodiment the system is comprised in a medical workstation or medical system, such as a Magnetic Resonance Imaging (MRI) System or Nuclear Magnetic Resonance (NMR) system.

The present invention according to some embodiments is not limited to the use of only two diffusion components. Any number of at least two or more diffusion components may be used. In this specification the two components are merely used for simplicity.

In some embodiments the discrete diffusion components of an investigated sample may be part of a continuous diffusion component function or diffusion component spectrum. In this case, by providing the filter block of the pulse sequence according to some embodiments, a part of the diffusion component spectrum will be masked instead of masking the second or fast diffusion component as mentioned for the discrete two-component model above.

The term "sample" used throughout this specification may e.g. be a sample comprising compartments having boundaries that may be of inorganic, organic synthetic and biological origin. Thus the term "sample" may comprise a zeolite as well as a liposome or a biological cell. Moreover the sample may comprise synthetic polymers, and may be of organic or inorganic origin.

Conditions for Embodiments According to the Invention

The following parameters D, $T_1$, $T_2$ and $G_{max}$ set the boundaries of the method according to some embodiments. D is the diffusion coefficient, $T_1$ is the longitudinal relaxation, $T_2$ is the transverse relaxation time and $G_{max}$ is the maximum field gradient.

The investigated molecule, such as water, may be studied provided that it contains an atomic nucleus with a nuclear spin other than 0.

The investigated molecule according to some embodiments must have a residing time within the boundary less than 10 s and at least 1 ms to assure that it has sufficient contact with the compartment boundaries. If it does not have sufficient contact with the boundaries it will not appear to be confined. Therefore, a fast diffusing molecule such as a molecule in gas phase or a small molecule in liquid phase may be studied when confined in a larger compartment than a slower diffusion molecule. For example, liquid water is perfectly studied when confined by a micrometer-sized compartment.

In some embodiments the distance the molecule moves in a time t is directly related to the diffusion coefficient D by: $<z^2>=2Dt$, where $<z^2>$ is the mean square displacement in $m^2$.

For example, if the diffusion coefficient is increased 4 times the compartment of study may be doubled under remaining good experimental conditions.

$T_1$ is limiting just as it is in normal diffusion experiments. If $T_1$ is too short the signal disappears. T1 shows for how long the signal can be stored. If $T_2$ is too short (as for larger molecules) the signal disappears during the application of the gradient pulses.

The field gradient $G_{max}$ is limiting since the time of the filter block depends on the gradient strength. With a weaker gradient a longer filter block is needed which eventually results in negative effects due to molecular exchange during the duration of the filter block.

Applications and use of the above described embodiments are various and the embodiments presented in this specification may be used for analytical purposes in vitro where there is an interest of knowing whether the diffusion of a molecule is restricted by a boundary and if so to what extent it is restricted, i.e. on which time scale it is restricted. For example, the study of the temperature dependence of the permeability of water molecules through yeast cell membranes.

Some embodiments of the invention are also particularly useful for studies of permeability, and may be used to characterize, study and modify confined compartments such as liposomes, cells, vesicles etc.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Diffusion Weighted NMR and MRI

The disclosure of some embodiments of the invention and the advantages of these are based on the description below with accompanying equations and the explanations thereof as well as FIGS. 10-20. The equations below have been given the numberings 1-32, although other equations without numbering have been presented previously in the description.

Figure 10:
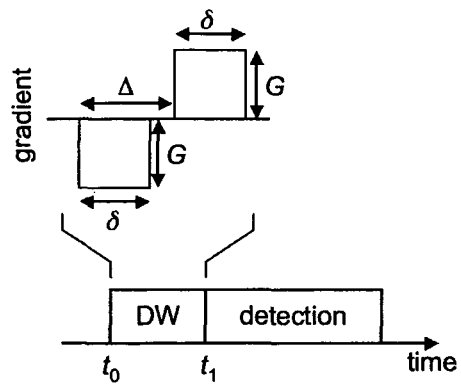

The commonly known general pulse sequence for diffusion weighted nuclear magnetic resonance (NMR) or magnetic resonance imaging (MRI) is shown in FIG. 10. A diffusion weighting (DW) block is inserted before the detection block, thereby inducing a molecular motion dependent attenuation of the intensity in each frequency channel for NMR, or for each pixel in MRI. The DW block in general consists of a pair of gradient pulses, most commonly being rectangular, trapezoidal, or sinusoidal in shape, separated by a refocusing 180° radiofrequency (RF) pulse inverting the phase shift induced by the previously applied gradient pulses. The first and second gradient pulse are denoted the defocusing and refocusing pulse, respectively. The simplest effective gradient shape is shown in the expansion in FIG. 10. Although an anti-symmetric effective gradient modulation is the most simple to implement in practice, strictly there is no requirement for such symmetry. A more general condition for refocusing is that the time integral of the effective gradient shape is zero at the end of the DW block. The sections below mostly refer to rectangular gradient pulses, but analogous expression can also be derived for other pulse shapes.

The detection block for NMR usually involves recording the time domain signal during free precession, which after Fourier transform (FT) yields an NMR spectrum. For MRI applications, the detection block consists of a single or a series of gradient or RF echoes, which upon FT yields 1D, 2D, or 3D images. Common detection schemes include, but are not limited to, echo planar imaging, fast spin echoes, spiral imaging, propeller imaging, etc. The signal attenuation of the DW block is commonly reported using the diffusion sensitizing variable b and the self-diffusion coefficient D by $$I = I_0 e^{-bD} \tag{1}$$

where I is the detected signal intensity and $I_0$ is the signal intensity at zero gradient strength. The b-value is calculated by $$b = \gamma^2 \int_{t_0}^{t_1} \left( \int_{t_0'}^{t'} G(t'') dt'' \right)^2 dt' \tag{2}$$

which for rectangular gradient pulses evaluates to $$b = (\gamma G \delta)^2 (\Delta - \delta/3), \tag{3}$$

where γ is the magnetogyric ratio, G is the amplitude of the gradients pulses, δ is the duration of the gradient pulses, and Δ is the separation between the leading edges of the gradient pulses.

D is related to the mean-square displacement $\langle Z^2 \rangle$ through $$\langle Z^2 \rangle = 2Dt \tag{4}$$

where t is the time interval over which diffusion is measured.

In the limit of short gradient pulses, where molecular displacements during the pulse is insignificant when compared to the displacements during the time between the pulses and the structural length scales of the system, $\langle Z^2 \rangle$ can be estimated from the signal attenuation induced by the DW block using $$I = I_0 e^{-2\pi^2 q^2 \langle Z^2 \rangle} \tag{5}$$

where q is the wave vector of the magnetization helix induced by the defocusing gradient pulse. The value of q is given by the area of the defocusing gradient pulse by $$q = \frac{\gamma}{2\pi} \int_0^{t_{1/2}} G(t') dt', \tag{6}$$

which equals $$q = \frac{\gamma G \delta}{2\pi} \tag{7}$$

for rectangular gradient pulses.

For systems with Gaussian diffusion, Eq. 5 is still valid if the estimated $\langle Z^2 \rangle$ refers to the displacement occurring during an effective diffusion time $t_d$ given by $$t_d = \Delta - \delta/3 \tag{8}$$

for rectangular gradient pulses. Even for systems with non-Gaussian diffusion, $\langle Z^2 \rangle$ can be estimated from the initial, low-q, attenuation of the signal under the condition of short gradient pulses as defined above. For the case of gradient pulses with finite length, one can define an apparent mean square displacement $\langle Z(\delta,\Delta)^2 \rangle$ and corresponding apparent diffusion coefficient $D(\delta,\Delta)$ from the initial, low-G, decay of $E = I/I_0$:

$$\langle Z(\delta, \Delta)^2 \rangle = -\frac{2}{\gamma^2 \delta^2} \lim_{G \to 0} \frac{\partial \ln E(G, \delta, \Delta)}{\partial G^2} \tag{9}$$

and $$D(\delta, \Delta) = \frac{\langle Z(\delta, \Delta)^2 \rangle}{2(\Delta - \delta/3)}. \tag{10}$$

Diffusion in a Spherical Cell

For a fluid with bulk diffusion coefficient $D_0$ confined in a spherical cavity with radius R, $\langle Z(\delta,\Delta)^2 \rangle$ can according to the present invention be shown to be $$\langle Z(\delta, \Delta)^2 \rangle = \tag{11}$$
$$4 \sum_{m=1}^{\infty} \frac{1}{\alpha_m^2 (\alpha_m^2 R^2 - 2)} \times \frac{2\alpha_m^2 D_0 \delta - 2 + 2e^{-\alpha_m^2 D_0 \delta} + 2e^{-\alpha_m^2 D_0 \Delta} - e^{-\alpha_m^2 D_0 (\Delta - \delta)} - e^{-\alpha_m^2 D_0 (\Delta + \delta)}}{(\alpha_m^2 D_0 \delta)^2}$$

where $\alpha_m$ are the roots of $$\alpha_m R J'_{3/2}(\alpha_m R) - \frac{1}{2} J'_{3/2}(\alpha_m R) = 0. \tag{12}$$

By making a series expansion of the exponentials in Eq. (11), the following useful limits are obtained:

$$\langle Z(\delta = 0, \Delta)^2 \rangle = 4 \sum_{m=1}^{\infty} \frac{1 - e^{-\alpha_m^2 D_0 \Delta}}{\alpha_m^2 (\alpha_m^2 R^2 - 2)}. \tag{13}$$

$$\langle Z(\delta, \Delta = \infty)^2 \rangle = 8 \sum_{m=1}^{\infty} \frac{1}{\alpha_m^2(\alpha_m^2 R^2 - 2)} \times \frac{\alpha_m^2 D_0 \delta - 1 + e^{-\alpha_m^2 D_0 \delta}}{(\alpha_m^2 D_0 \delta)^2}. \tag{14}$$

$$\langle Z(\delta = 0, \Delta \ll R^2/D_0)^2 \rangle = 2D_0 \Delta \tag{15}$$

$$\langle Z(\delta = 0, \Delta = \infty)^2 \rangle = \frac{2}{5} R^2. \tag{16}$$

$$\langle Z(\delta \gg R^2/D_0, \Delta = \infty)^2 \rangle = \frac{8R^4}{D_0 \delta} \sum_{m=1}^{\infty} \frac{1}{\alpha_m^4 R^4 (\alpha_m^2 R^2 - 2)} \approx \frac{0.183 R^4}{D_0 \delta}. \tag{17}$$

Eq. (11) is plotted in FIG. 11. The restricted and non-restricted cases coincide at short $t_d$. For the restricted case, an upper limit is reached at long $t_d$ and short δ. When the DW block is used as a filter to remove the signal from non-restricted components, δ and Δ should chosen to maximize the difference of $\langle Z(\delta, \Delta)^2 \rangle^{1/2}$ between the free and restricted components, while keeping δ and Δ much shorter than the characteristic time for exchange between the components. The equations above make a rational design of DW filters according to the present invention possible.

Molecular Exchange Between Extra- and Intracellular Components

Figure 12:
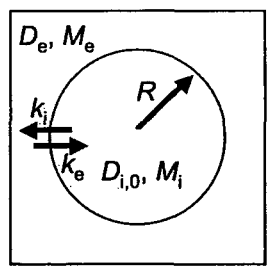

A simple model of biological tissue, consisting of a spherical cell with radius R in a surrounding medium, is shown in FIG. 12. The ratio between the number of molecules in the intra- and extracellular compartments, $n_i$ and $n_e$, is the equilibrium constant K:

$$K = \frac{n_e}{n_i}. \tag{18}$$

Self-diffusion in the intra- and extracellular fluids occur with the diffusion coefficients $D_{i,0}$ and $D_e$. For convenience, the effects of obstruction of the extracellular fluid originating from the presence of the spherical cells are included in $D_e$. The effective diffusion coefficient $D_i$ of the intracellular fraction depends on the values of δ and Δ according to Eqs. (10) and (11). Molecular exchange takes place across the cell membrane with permeability P. The outward and inward exchange rates $k_i$ and $k_e$ are given by $$k_i = 3P/R \tag{19}$$

and $$k_e = \frac{k_i}{K}. \tag{20}$$

The exchange rates are related to the mean residence times in the intra- and extracellular phases, $\tau_i$ and $\tau_e$, via $$\tau_i = 1/k_i$$

$$\tau_e = 1/k_e. \quad (21)$$

Using a macroscopic approach, the signal attenuation during the DW block can be calculated by solving the differential equation $$\frac{dM_i}{dt} = -4\pi^2 q^2 D_i - k_i M_i + k_e M_e \quad (22)$$

$$\frac{dM_e}{dt} = -4\pi^2 q^2 D_e + k_i M_i - k_e M_e.$$

for the magnetizations in the intra- and extracellular phases, $M_i$ and $M_e$, using the initial condition $$M_{i,0} = \frac{M_0}{1+K} \quad (23)$$

$$M_{e,0} = \frac{M_0}{1+K^{-1}}$$

where is $M_0$ the total magnetization at equilibrium. Eq. (22) assumes Gaussian diffusion in the two phases with the diffusion coefficients $D_i$ and $D_e$. Exchange between the two phases occur with the rate constants $k_i$ and $k_e$. In Eq. (22), there is no reference to the microscopic geometry of the system. Within the short gradient pulse approximation, the solution to Eq. (22) for the intra- and extracellular magnetizations $M_{i,1}$ and $M_{e,1}$, at the time $t_1$ is $$M_{i,1} = \frac{1}{2}\left(M_{i,0} - \frac{BM_{i,0} - k_e M_{e,0}}{C}\right)e^{-(A-C)\Delta} + \quad (24)$$
$$\frac{1}{2}\left(M_{i,0} + \frac{BM_{i,0} - k_e M_{e,0}}{C}\right)e^{-(A+C)\Delta}$$

$$M_{e,1} = \frac{1}{2}\left(M_{e,0} + \frac{BM_{e,0} + k_i M_{i,0}}{C}\right)e^{-(A-C)\Delta} + $$
$$\frac{1}{2}\left(M_{e,0} - \frac{BM_{e,0} + k_i M_{i,0}}{C}\right)e^{-(A+C)\Delta}$$

where $$A = 2\pi^2 q^2 (D_i + D_e) + \frac{k_i + k_e}{2} \quad (25)$$

$$B = 2\pi^2 q^2 (D_i - D_e) + \frac{k_i - k_e}{2}$$

$$C = \sqrt{B^2 + k_i k_e}$$

The total NMR signal is proportional to the sum of $M_i$ and $M_e$ and the ratio $I/I_0$ equals $(M_{i,1}+M_{e,1})/(M_{i,0}+M_{e,0})$.

Figure 13:
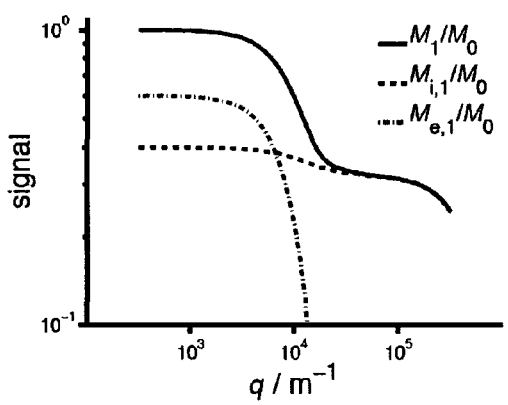

The following modifications of Eq. (24) are performed according to the present invention to make it valid also for exchange between a spherical cell and a continuous medium and having gradient pulses of finite length: $D_i$ is calculated with Eqs (10) and (11) and $\Delta$ in the exponentials are replaced with $t_d$. This modification is expected to be accurate as long as $\delta \ll \tau_i, \tau_e$. An example of $M_{i,1}$ and $M_{e,1}$ vs. q is shown in FIG. 13. As is evident from FIG. 14, the derived expression accurately describes the diffusion weighting for water in a packed sediment of yeast cells over a wide range of values of $\delta$ and $\Delta$. Fitting Eq. (24) to experimental data yields estimates of the time scale for exchange, but this approach is not practical for clinical application since the dependence of the experimentally observed signal intensities on the exchange time is rather weak.

DW Filter: Removing the Extracellular Signal

Figure 15:
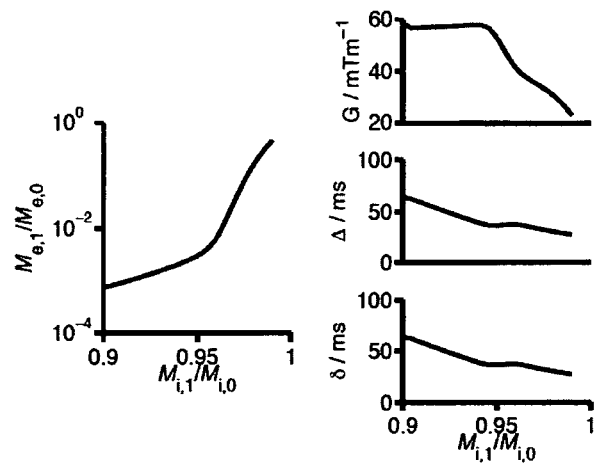

Using the model according to the present invention described above and reasonable assumptions about the values of $D_{i,0}$, $D_e$, R, K, and P, it is possible make a judicious choice of a $\{\delta, \Delta, G\}$ parameter set designed to remove the signal originating from the extracellular component while keeping the signal from the intracellular one. More efficiently, an iterative numerical procedure can be used to find the set $\{\delta, \Delta, G\}$ that minimizes the signal from the extracellular component for a given attenuation of the intracellular one. An example of such an optimization is shown in FIG. 15. Note that the optimum values of $\{\delta, \Delta, G\}$ are within the range of instrumentally feasible values for a top-end clinical MRI system.

Numerical methods can be used according to the invention to solve Eq. (22) when the condition $\delta \ll \tau_i, \tau_e$ is not fulfilled or if the gradient modulation is more complicated than the rectangular one depicted in FIG. 10. The theoretical description of the effect of the DW filter according to the present invention above is in some cases essential for a rational design.

Diffusion-Diffusion Exchange

Figure 16:
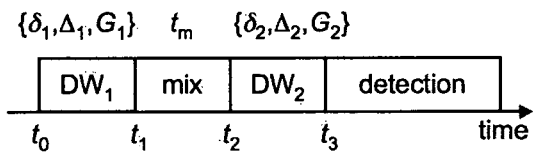

A schematic picture of the pulse sequence to encode NMR or MRI for molecular exchange between components with fast and slow diffusion is displayed in FIG. 16. Two diffusion weighting blocks, $DW_1$ and $DW_2$, separated by a mixing block with duration $t_m$ or $t_{mix}$, precede signal detection. Each DW block in FIG. 16 obey the same constraints and can be analyzed in a similar way as the DW block in FIG. 10. The time points $t_0$, $t_1$, $t_2$, and $t_3$ are indicated in the figure. For each of these time points $t_n$, one can estimate the amplitudes of the intracellular, extracellular, and total magnetizations $M_{i,n}$, $M_{e,n}$ and $M_n = M_{i,n} + M_{e,n}$, respectively. The change of the magnetizations during the time period between $t_0$ and $t_1$ is given by Eq. (24).

Neglecting nuclear relaxation processes, the effect of the mixing block is to redistribute the magnetization between the intra- and extracellular components, while preserving the overall magnitude of the total magnetization, i.e. $M_2 = M_1$. The relative contributions to the total magnetization after the mixing time can be shown to be $$\frac{M_{i,2}}{M_2} = \frac{M_{i,0}}{M_0} - \left(\frac{M_{i,0}}{M_0} - \frac{M_{i,1}}{M_1}\right)e^{-(k_i+k_e)t_m} \quad (26)$$

$$\frac{M_{e,2}}{M_2} = \frac{M_{e,0}}{M_0} - \left(\frac{M_{e,0}}{M_0} - \frac{M_{e,1}}{M_1}\right)e^{-(k_i+k_e)t_m}.$$

The evolution of the magnetizations $M_i$ and $M_e$ during the $DW_2$ block, the time period between $t_2$ and $t_3$, is again given by Eq. (24). Thus, $M_{i,3}$ and $M_{e,3}$ can be calculated by application of Eq (24), then Eq. (26), and finally Eq (24) again according to the present invention. The theoretical expression for the signal after the $DW_1$-mix-$DW_2$ sequence may be essential for a rational design of new protocols according to the present invention, as described below.

Generalization

The analysis above has for simplicity been focused on exchange between two components: one freely diffusing and one confined in a spherical cavity with a permeable membrane. Those skilled in the art will realize that the analysis above, and the protocols to be presented below, can be generalized to other geometries, number of components, and gradient modulation schemes.

Callaghan's Protocols

The same general pulse sequence as the one shown in FIG. 16 was previously introduced by Callaghan (Callaghan, Furó. J. Chem. Phys. 2004, 120, 4032). The method according to Callaghan is performed in the following way:

1) Keep $\delta_4=\delta_2$, $\Delta_1=\Delta_2$, and $t_m$ constant, vary $G_1$ and $G_2$ independently (typically in 16×16=256 separate steps), and perform a 2D inverse Laplace transform. The presence of "cross peaks" in the thus obtained diffusion-diffusion exchange 2D correlation spectrum indicates exchange on the time-scale of the $t_m$.

2) Repeat the protocol described in 1) for a series of $t_m$ (typically 4 or 8, thus yielding 16×16×8=2048 separate steps). A numerical estimate of $(k_i+k_e)$ is obtained by analysis of the variation of the volume of the cross peaks as a function of $t_m$.

New Protocols According to the Present Invention

Figure 17:
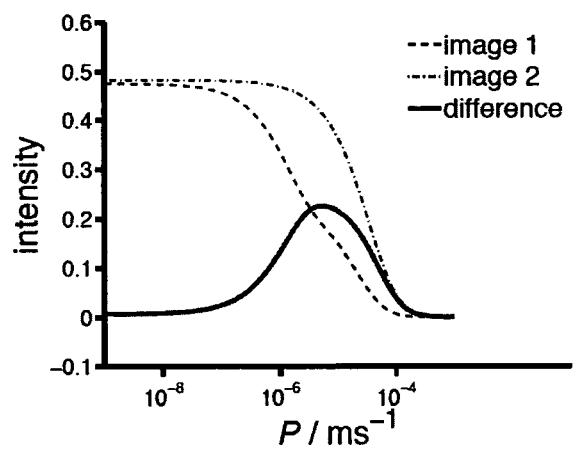

The protocols proposed here differ from the ones introduced by Callaghan in the way the parameters describing each DW block are varied and the way of analyzing the data, thereby leading to orders of magnitude shorter experiment time for the same information content. This reduction in experiment time is crucial for the practical implementation in a clinical setting. Herein we suggest the following protocols:

1) Find a set of $\{\delta_1,\Delta_1,G_1\}$ to reduce the extracellular component as much as possible without affecting the intracellular one (e.g. by an educated guess or a numerical procedure). Find a set of $\{\delta_2,\Delta_2, G_2\}$ to completely reduce the extracellular component while retaining as much as possible of the intracellular one. Choose a reasonable mixing time $t_m$ based on the expected exchange rate and the nuclear relaxation times. Record image 1 using the parameters $\{\delta_1,\Delta_1,G_1,t_m,\delta_2,\Delta_2,G_2\}$ and image 2 with $\{(\delta_1,\delta_1,G_1=0,t_m,\delta_2,\Delta_2,G_2\}$. As shown in FIG. 17, the difference image obtained by subtracting image 1 from image 2 yields signal intensity only if there is molecular exchange on the time scale defined by the experimental variables. This protocol gives the same information as Callaghan 1) above at more than 100 times shorter experiment time.

2) Repeat the protocol described in 1) for a series of $t_m$. A numerical estimate of $k_i+k_e$ is obtained by analysis of the variation of the signal intensity as a function of $t_m$. Once again, this protocol gives the same information as Callaghan 2) above at more than 100 times shorter experiment time.

3) Repeat a protocol with $\{\delta_1,\Delta_1,G_1,t_m,\delta_2,\Delta_2,G_2\}$ for a series of $G_2$ and $t_m$ (typically 16×7=116 separate steps). Complement with a series of $G_2$ at the smallest value of $t_m$ and using $G_1=0$ (typically 16 steps). This latter series improves the accuracy of the estimated parameters according to the present invention. Analysis according to the following section yields estimates of $k_i$, $k_e$, and K. Experimental demonstrations of this protocol are shown in FIG. 18 and FIGS. 19A and 19B.

Data Evaluation

While the data evaluation required for protocols 1) and 2) are trivial taking the difference between two images and exponential fitting to a series of difference images, respectively—the evaluation of protocol 3) is somewhat less straightforward. The more advanced analysis is more than well justified by estimating parameters that are directly related to the cellular microstructure and dynamics, instead of the more phenomenological parameters of the new protocols 1) and 2) and Callaghan's protocols.

Figure 18:
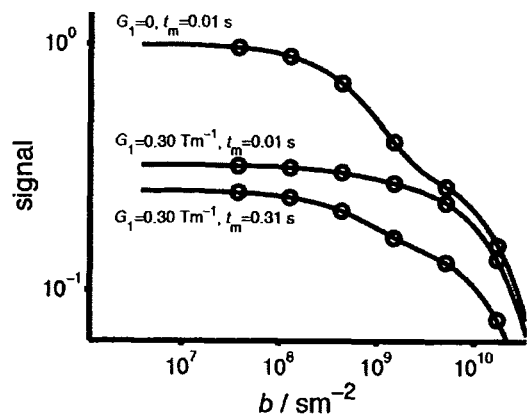
Figure 19:
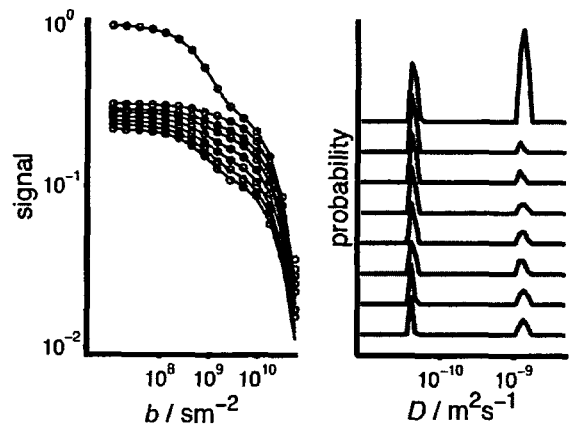
Figure 19:
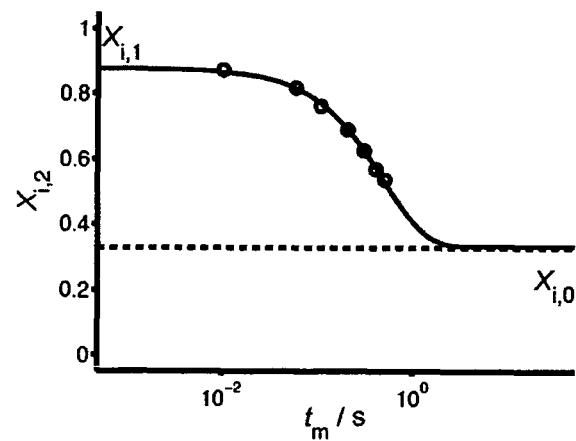

Experimental data for water in a yeast cell sediment is shown in FIG. 18. In this system there is a clear difference between a slow (intracellular) and fast (extracellular) component in the plot of NMR signal vs. b, defined in Eq. (2), when the $DW_1$ block is turned off ($G_1=0$). This data series is equivalent to what would be obtained with infinitely long $t_m$ ($t_{mix}$). Such a measurement is impossible to perform in practice since the signal would be reduced below the noise level because of nuclear relaxation processes. The fast component disappears when turning the $DW_1$ block on ($G_1=0.30$ Tm$^{-1}$). Increasing $t_m$ leads to the reappearance of the fast component on expense of the slow one. This observation is an unambiguous indication of molecular exchange between the intra- and extracellular components.

For data fitting purposes it is according to the present invention convenient to rewrite Eqs (24) to (26) as $$I_n(b)=I_{0,n}(X_{i,n}e^{-bD_i}+X_{e,n}e^{-bD_e}) \quad (27)$$

where $$X_{i,n}=X_{i,0}-(X_{i,0}-X_{i,1})e^{-kt_{m,n}} \quad (28)$$

and $$X_{e,n}=1-X_{i,n}. \quad (29)$$

According to the invention, the data series with different $t_m$ are labeled with the index n. As justified above, the series with $G_1=0$ is treated as a series with $t_m=\infty$. In Eq. (27), b refers to the $DW_2$ block. Replacing Eq. (24) with a biexponenial as in Eq. (27) is an approximation which is expected to be good as long as $\tau_i$ and $\tau_e$ are much longer than $\delta$ and $\Delta$ in each DW block. Eq. (27) with Eqs. (28) and (29) are fitted to the entire set of experimental data using $D_i$, $D_e$, k, $X_{i,0}$, $X_{i,1}$ and the set of $I_{0,n}$ as adjustable parameters. The system parameters K and $k_i$ are related to the fit parameters k and $X_{i,0}$ through $$K = \frac{1-X_{i,0}}{X_{i,0}} \quad (30)$$

and $$k_i = \frac{k}{1+K^{-1}}. \quad (31)$$

An example of the described data fitting procedure is shown in FIG. 18. A global fit according to the present invention as described above yields the most accurate results of the estimated parameters.

For systems that are more complicated than yeast cell sediments, the biexponential function in Eq. (27) can be replaced with other multiexponential expressions. Alternatively, one can relate the signal $I_n(b)$ to a diffusion coefficient distribution $P_n(D)$ through $$I_n(b) = \int_0^\infty P_n(D)e^{-bD}dD. \quad (32)$$

$P_n(D)$ can be estimated from the experimental $I_n(b)$ using an inverse Laplace transform (ILT) algorithm. The variation of the amplitudes of the various components in the obtained $P_n(D)$ as a function of $t_m$ can be analyzed for exchange using equations analogous to Eq. (28). Unfortunately ILT algorithms are notorious for their instability, leading to sometimes wildly fluctuating positions of the peaks in $P_n(D)$. According to the present invention, this problem was solved by a customized ILT algorithm where the peak positions (but not the amplitudes) were enforced to be constant for all series with different $t_m$. Imposing the constraint of fixed peak positions for all $P_n(D)$ improves the accuracy of the estimated parameters. For each $P_n(D)$, $X_{i,n}$ is evaluated by integrating the areas of the peaks corresponding to the intra- and extracellular components. In a subsequent step, k, $X_{i,0}$, and $X_{i,1}$ are estimated by fitting Eq. (28) to the data. An example of the described procedure is shown in FIGS. 19A and 19B. The estimated parameters agree favourably with the results of the previously described global fitting procedure. The ILT method of analysis is more general than the global fitting, but in order to improve the numerical stability more data points and consequently longer experiment time is required.

Figure 20:
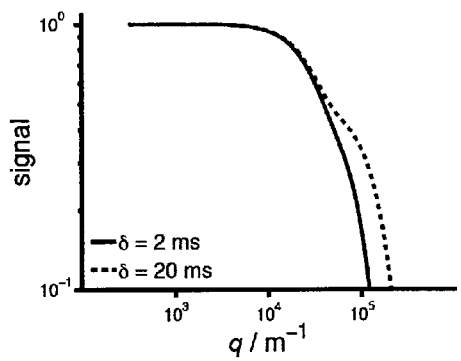

In order to increase the accuracy of the estimated $X_{i,2}$, the different diffusion statistics of the intra- and extracellular components can be utilized according to the present invention. As shown in FIG. 20, acquiring data for at least two different values of δ while keeping $t_d$ constant facilitates separation of the free and restricted components.

Description of FIGS. 10-20 in Relation to the Summary Above Referring to New Protocols of the Present Invention FIG. 10 shows a schematic of a pulse sequence to encode an NMR spectrum or MR image for molecular diffusion. The signal intensity is attenuated by a diffusion weighting block, DW, preceding signal detection. The DW block consists of a pair of gradient pulses of duration δ and amplitude G, having the opposite effective polarity. Δ is the time between the onset of the gradient pulses. The time points in the beginning and the end of the DW block are labeled $t_0$ and $t_1$, respectively.

Figure 11:
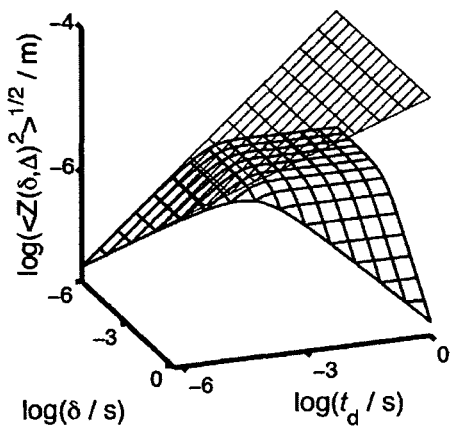

FIG. 11 shows the apparent root-mean-square displacement $<Z(\delta,\Delta)^2>^{1/2}$ vs. gradient pulse length δ and effective diffusion time $t_d=\Delta-\delta/3$ calculated with Eq. (11) for a liquid with bulk self-diffusion coefficient $D_0=2\cdot10^{-9}$ m$^2$s$^{-1}$ confined in a spherical pore with radius R=2.5 μm (thick lines) or diffusing without restricting boundaries (thin lines).

FIG. 12 shows a model for molecular exchange between a spherical cell and the surrounding medium. The model is described with the following parameters: diffusion coefficient of the intracellular fluid $D_{i,0}$, diffusion coefficient in the extracellular medium $D_e$, cell radius R, cell membrane permeability P, and the intra- and extracellular magnetizations, $M_i$ and $M_e$. The outward and inward exchange rates, $k_i$ and $k_e$, are related to P, R, and K through Eqs. (19) and (20).

FIG. 13 shows the diffusion NMR signal at the time $t_1$ vs. wave vector q calculated with Eq. (24) for a system with intracellular diffusion coefficient $D_{i,0}=1\cdot10^{-9}$ m$^2$S$^{-1}$, extracellular diffusion coefficient $D_e=1.5\cdot10^{-9}$ m$^2$S$^{-1}$, equilibrium constant K=1.5, cell radius R=2.5 μm, and cell membrane permeability $P=1\cdot10^{-6}$ ms$^{-1}$. The calculations were performed for the following pulse sequence parameters: δ=50 ms, Δ=200 ms, and maximum G=150 mTm$^{-1}$. The lines show the intra- and extracellular components $M_{i,1}$ and $M_{e,1}$, and their sum $M_1$.

Figure 14:
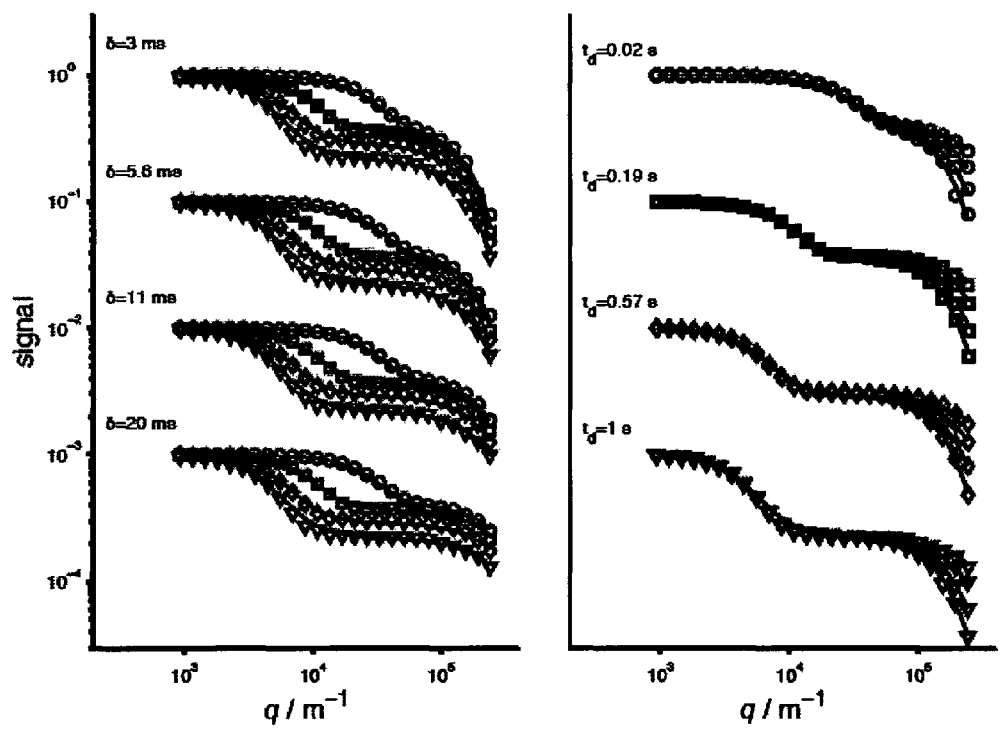

FIG. 14 shows the diffusion NMR signal vs. wave vector q for water in a sediment of yeast cells. Data was recorded for 16 different combinations of effective diffusion times $t_d$ and gradient pulse lengths δ (see for definitions). Symbols are experimental data and the lines are the results of a global fit of Eq. (24), yielding the intracellular diffusion coefficient $D_i=8\pm2\cdot10^{-10}$ m$^2$s$^{-1}$, extracellular diffusion coefficient $D_e=1.40\pm0.02\cdot10^{-9}$ m$^2$S$^{-1}$, equilibrium constant K=1.42±0.03, cell radius R=2.4±1 μm, and cell membrane permeability P=5.3±0.3·10$^{-7}$ ms$^{-1}$ (confidence interval 67% using Monte Carlo error estimation). The same data, with identical symbols, is shown in both the left and the right panels. In the left (right) panel the data is vertically displaced according to the value of δ($t_d$) in order to highlight the trends when varying $t_d$(δ).

FIG. 15 shows the numerical optimization of the DW block for a system with $D_{i,0}=1\cdot10^{-9}$ m$^2$s$^{-1}$, $D_e=1.5\cdot10^{-9}$ m$^2$s$^{-1}$, K=1, R=2.5 μm, and $P=1\cdot10^{-6}$ ms$^{-1}$. $M_{i,1}$ and $M_{e,1}$ were calculated with Eq. (24). The minimum value of $M_{e,1}/M_{e,0}$, i.e. a maximal reduction of the extracellular signal, for a given value of $M_{i,1}/M_{i,0}$ is shown in the left panel. The panels to the right display the optimum values of δ, Δ, and G.

FIG. 16 shows a schematic of a pulse sequence to encode the NMR spectrum or MR image for molecular exchange between components with slow and fast diffusion. Two diffusion weighting blocks, $DW_1$ and $DW_2$, are separated by a mixing block with duration $t_m$. Each DW block is similar to the expansion shown in FIG. 10. The evolution of the intra- and extracellular magnetizations $M_i$ and $M_e$ between time points $t_0$-$t_1$, $t_1$-$t_2$, and $t_2$-$t_3$ can be calculated with Eq. (24), (26), and (24), respectively.

FIG. 17 shows the calculated diffusion exchange contrast for the pulse sequence in FIG. 16 using the parameters $\delta_1=\Delta_1=38$ ms, $\delta_2=\Delta_2=41$ ms, and $t_m=0.3$ s for systems with intracellular diffusion coefficient $D_{i,0}=1\cdot10^{-9}$ m$^2$S$^{-1}$, extracellular diffusion coefficient $D_e=1.5\cdot10^{-9}$ m$^2$S$^{-1}$, and equilibrium constant K=1. The figure shows the image intensity as a function of cell membrane permeability P for $G_1=38.9$ mTm$^{-1}$ and $G_2=59.6$ mTm$^{-1}$ (image 1) and $G_1=0$ mTm$^{-1}$ and $G_2=59.6$ mTm$^{-1}$ (image 2). The difference between these images yields image intensity only if there are both slow and fast diffusion components, and there is molecular exchange between the components on the time scale of $t_m$.

FIG. 18 shows the NMR signal vs b for the diffusion exchange experiment applied to water in a yeast cell sediment using the parameters $\delta_1=\delta_2=5.2$ ms, $\Delta_1=\Delta_2=15.4$ ms, and max $G_2=0.81$ Tm$^{-1}$. The values of b refer to the $DW_2$ block in FIG. 16. Experimental data are shown as circles and the results of a global fit of Eq (27) with Eqs. (28) and (29) as lines. The values of $G_1$ and $t_m$ used for the different sets of data are indicated in the figure. The fit yields the following results: effective exchange rate $k=(k_i+k_e)=1.96\pm0.08$ s$^{-1}$, apparent intracellular diffusion coefficient $D_i(\delta,\Delta)=4.8\pm0.3\cdot10^{-11}$ m$^2$S$^{-1}$, extracellular diffusion coefficient $D_e=1.36\pm0.02\cdot10^{-9}$ m$^2$S$^{-1}$, intracellular fraction at equilibrium $X_{i,0}=M_{i,0}/M_0=0.335\pm0.003$ and intracellular fraction after the $DW_1$ block $X_{i,1}=M_{i,1}/M_1=0.903\pm0.008$.

FIGS. 19A and 19B show the Inverse Laplace Transform analysis of the diffusion exchange experiment. Experimental parameters are the same as in FIG. 18, with the exception that many more data points in both the $G_2$ and $t_m$ dimensions were acquired. (a) NMR signal vs b and corresponding probability distributions of diffusion coefficients. Experimental data points are shown as circles in the left panel. The diffusion coefficient distributions obtained with a constrained ILT algorithm are shown in the right panel. The lines in the left panel are calculated from the distributions. (b) Intracellular fraction after the mixing block $X_{i,2}=M_{i,2}/M_2$ as a function of $t_m$. The circles and the dashed line are calculated from the areas of the peaks in (a), while the line represents a fit of Eq. (28) to the data. The fit yields the following results: effective exchange rate $k=(k_i+k_e)=2.01$ s$^{-1}$, intracellular fraction at equilibrium $X_{i,0}=M_{i,0}/M_0=0.333$ and intracellular fraction after the $DW_1$ block $X_{i,1}=M_{i,1}/M_1=0.878$.

FIG. 20 show an improved resolution of intra- and extracellular components by varying the gradient pulse length δ while keeping the effective diffusion time $t_d$ constant. Calculations were performed using Eq (24) for a system with $D_{i,0}=1\cdot10^{-9}$ m$^2$S$^{-1}$, $D_e=1.5\cdot10^{-9}$ m$^2$S$^{-1}$, K=1, R=4 μm, and $P=1\cdot10^{-6}$ ms$^{-1}$. The pulse programs parameters are $t_d=20$ ms and $\delta=2$ (solid) and 20 (dashed) ms.

Figure 21:
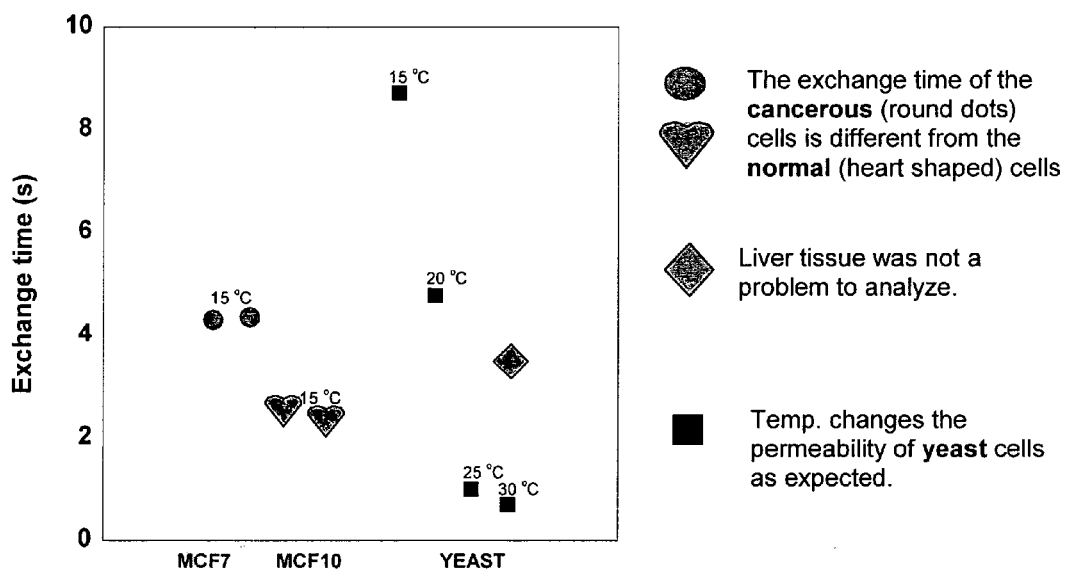

Description of Some Trials as Well as Related FIG. 21

Example Related to Yeast Cells

For preparing the samples used in the measurements, distilled water and ordinary bakers yeast were used. The yeast was used without any preprocessing. A solution of yeast and water (in approximately 1:1 weight proportions) was made and poured into 5 mm NMR tubes. It was then left in a fridge for the yeast to sediment (for at least six hours). Fresh samples were prepared each day because of small gas bubbles that would gather in the older samples and were thought to influence the readings. Subsequently, a portion of dense solution was carefully transferred, with the use of a Pasteur pipette, to a Shigemi tube (Sigma Aldrich, USA), which was used in the measurements.

A 5 mm Shigemi tube was used for the measurements to ensure that the sample is entirely enclosed within a homogenous magnetic field. Simultaneously, the glass bottom of the outer tube and the glass insert are sure to not give any signal in the measurements, therefore one can be ensured that the whole obtained reading comes from the investigated sample. Consequentially, it also enables the use of a smaller amount of the sample for the measurements, while not having an interphase within the volume inserted into the coil.

A Bruker DMX-200 MHz NMR spectrometer was used to perform the measurements. The probe used was a diffusion probe with a 5 mm RF coil. The maximum gradient strength was 9.63 T and the temperature control unit of the probe had the accuracy of 0.5° C.

Diffusion experiments were performed with the use of a spin echo diffusion pulse program. A version of the sequence, having a constant gradient amplitude in the first diffusion sequence, was used.

A set of experiments was carried out for few temperatures (5, 15, 20, 25, 30 and 35° C.). Each sequence was begun with a diffusion experiment for a given temperature, in order to determine the strength of the first gradient that was required to "kill" the signal from the fast moving water. When that was decided, the constant gradient was set and a series of experiments was carried out. For each (experiment), the mixing time was increased in order to determine the speed with which the water molecules escaped the yeast cells. After the acquisition parameters were set for a series of experiments the mixing time was the only one to be changed. All the other parameters were kept constant to ensure the comparability of the experiments. Also—the parameters were kept constant throughout the different series of experiments, to make the obtained data more comparable.

The initial gradient in each experiment was established to be 70% of the maximum for all the experiments. For each of the temperatures multiple experiments were carried out—each with a different mixing time.

The resulting exchange times are displayed in FIG. 21. The non-invasive method to study the permeability of living cells according to the present invention is much faster and more accurate than methods according to state of the art. The advantage of studying a non-disturbed system according to the present invention is of great value for pharmaceutical and medical purposes.

Example Related to Human Cells

The MCF-7 (HTB-22) and MCF-10A (CRL-10317) cell lines were purchased from American Type Culture Collection, Manassas, Va., USA. All cell lines were cultured at 37° C., in a humidified incubator with 5% $CO_2$ in air. MCF-7 cells were cultured in RPMI 1640 medium supplemented with 10% fetal calf serum (FCS), non-essential amino acids, insulin (10 µg/ml), antibiotics (50 U/ml penicillin and 50 mg/ml streptomycin). The MCF-10A cells were cultured in RPMI 1640 medium supplemented with 10% heat-inactivated FCS, non-essential amino acids, insulin (10 µg/ml), epidermal growth factor (20 ng/ml), cholera toxin (50 µg/ml), hydrocortisol (1 mg/ml), penicillin (50 U/ml), and streptomycin (50 mg/ml). Medium components were purchased from Biochrom, Berlin, Germany, and Sigma-Aldrich, Stockholm, Sweden. Tissue culture plastics were purchased from Nunc, Roskilde, Denmark. For the experiments, a number of replicate cultures, consisting of $5\times10^6$ cells seeded into 10 ml medium in bacteriological Petri dishes (9 cm diameter), were set up. One day after seeding, the cells that had attached to the bottom were dislodged by scraping with a rubber police man. The cells were further incubated for 48-72 hours before harvesting. The spheroids and aggregates that had formed were dislodged from the bottom by careful scraping and the pipetted together with the medium to a sterile 50 ml tube. The cells were pelleted by centrifugation at 500 g for 6 min at room temperature. Thereafter the medium was aspirated and the cells resuspended in a small volume of phosphate-buffered saline (PBS, 8 g/L NaCl, 0.2 g/L KCl, 1.15 g/L $Na_2HPO_4$, 0.2 g/L $KH_2PO_4$, pH 7.3, purchased from Oxoid Ltd., Basingstoke, Hampshire, UK) containing 10% FCS, 2.5 gr/liter glucose, Na-pyruvate, non-essential aminoacids, penicillin (50 U/ml), and streptomycin (50 mg/ml). The cells were kept on ice before MR analysis. Approximately $10^7$ cells were used for each analysis.

The suspensions were transferred to a Shigemi-tube. After the piston was put in place (making sure no bubbles were present) the sample was put into a Bruker DMX-200 spectrometer, operating at 200.13 MHz proton resonance frequency. The pulse-field-gradients were generated by a Bruker Diff 25 gradient probe driven by a BAFPA-40 unit. For each experiment an ordinary PFG-SE-experiment was done to confirm the presence of domains with different diffusion coefficient, to determine a proper choice of gradient strength for the filtering spin echo in the filter block and to get appropriate limits for the fitting procedure. For these experiments $\delta$ was set to 1 ms, $\Delta$ was set to 38.1 ms and the gradient strength varied logarithmically between 0.3 to 9.63 T/m. When the diffusion measurement was done a series of experiments were preformed with an increase in the mixing time for each new experiment. 18 different mixing times were used. All other parameters were kept constant ($\delta=0.6$ ms, $\Delta=18.2$ ms, $g_{filter}=6.7$ T/m and $g_{diff}$ changed, logarithmically, from 0.30 to 9.63 T/m).

The resulting exchange times are displayed in FIG. 21. The non-invasive method to study the permeability of living cells according to the present invention is much faster and more accurate than methods according to state of the art. The advantage of studying a non-disturbed system according to the present invention is of great value for pharmaceutical and medical purposes.

Example Related to Liver Tissue

The liver was removed by dissection from a healthy NMRI mouse killed by for other purposes (ethical permit held by Prof. Martin Kanje, Department of Cell and Organism Biology, Lund University). The liver was immediately washed with and then immersed in ice-cold phosphate-buffered saline containing 5% fetal calf serum, 1 mM non-essential amino acids, and 1 mM sodium pyruvate. The liver was then carefully dissected into lobules which were kept in this solution on ice until use.

The sample was transferred to a Shigemi-tube. After the piston was put in place (making sure no bubbles were present) the sample was put into a Bruker DMX-200 spectrometer, operating at 200.13 MHz proton resonance frequency. The pulse-field-gradients were generated by a Bruker Diff-25 gradient probe driven by a BAFPA-40 unit. For each experiment an ordinary PFG-SE-experiment was done to confirm the presence of domains with different diffusion coefficient, to determine a proper choice of gradient strength for the filtering spin echo in the filter block and to get appropriate limits for the fitting procedure. For these experiments δ was set to 1 ms, Δ was set to 38.1 ms and the gradient strength varied logarithmically between 0.3 to 9.63 T/m. When the diffusion measurement was done a series of experiments were preformed with an increase in the mixing time for each new experiment. 18 different mixing times were used. All other parameters were kept constant (δ=0.5 ms, Δ=20.3 ms, $g_{filter}$= 6.7 T/m and $g_{diff}$ changed, logarithmically, from 0.30 to 9.63 T/m).

The resulting exchange times are displayed in FIG. 21. The non-invasive method to study the permeability of living cells according to the present invention is much faster and more accurate than methods according to state of the art. The advantage of studying a non-disturbed system according to the present invention is of great value for pharmaceutical and medical purposes.

DESCRIPTION OF SOME EMBODIMENTS OF THE PRESENT INVENTION

According to one embodiment of the present invention there is provided a method (70) for magnetic resonance imaging or nuclear magnetic resonance spectroscopy comprising: emitting (71) a radio frequency pulse sequence towards an object being subjected to a magnetic field, wherein said object comprises a molecule having an atom with a nuclear spin differing from 0,
emitting (72) a gradient pulse sequence towards said object, detecting (73) and acquiring a magnetic resonance signal from said object corresponding to said emitted radio frequency pulse sequence, wherein said gradient pulse sequence comprises a first diffusion weighting block with an amplitude $G_1$, a mixing block with duration $t_{mix}$ and a second diffusion weighting block with an amplitude $G_2$, wherein all of $G_1$, $t_{mix}$ and $G_2$ are either varied, fixed or in on or off mode and at least one of $G_1$ or $G_2$ is fixed or in on or off mode.

The processing according to present invention has an advantage over the Callaghan protocol in view of the fact that the same information obtained by an experiment run according to Callaghan may be obtained much faster according to the present invention, such as with 10, 100 or even more times shorter experiment time.

By the term "in on or off mode" is herein meant that a parameter in on or off mode may in such a case only have two values, either zero, i.e. off, or something else, i.e. on.

According to one specific embodiment of the present invention, the gradient pulse sequence comprises a first diffusion weighting block with an amplitude $G_1$, a mixing block with duration $t_{mix}$ and a second diffusion weighting block with an amplitude $G_2$, wherein one of the following is valid:

$G_1$ is in on or off mode, $G_2$ is fixed and $t_{mix}$ is fixed;
$G_2$ is in on or off mode, $G_1$ is fixed and $t_{mix}$ is fixed;
$G_1$ is in on or off mode, $G_2$ is fixed and $t_{mix}$ is varied;
$G_2$ is in on or off mode, $G_1$ is fixed and $t_{mix}$ is varied;
$G_1$ is fixed, $G_2$ is varied and $t_{mix}$ is varied, which is complemented by a series where $G_1$ equals zero, $t_{mix}$ is fixed and $G_2$ is varied; or
$G_2$ is fixed, $G_1$ is varied and $t_{mix}$ is varied, which is complemented by a series where $G_2$ equals zero, $t_{mix}$ is fixed and $G_1$ is varied.

In the case of $G_1$ being in on or off mode, $G_2$ and $t_{mix}$ being fixed it is according to present invention possible to achieve a difference image and thereby information regarding if there is an exchange or not just by doing a series of trials according to (2×1×1), i.e. two trials (see FIG. 17).

As another example, in the case of $G_1$ being in on or off mode, $G_2$ being fixed and $t_{mix}$ being varied it is according to present invention possible to achieve a series of difference images and thereby the exchange rate ($k_i+k_e$).

As yet another example, in the case of $G_1$ being fixed, $G_2$ being varied and $t_{mix}$ being varied, and then a complemented series where $G_1$ equals zero, $t_{mix}$ is fixed and $G_2$ is varied it is according to the present invention possible to achieve the exchange rate $k_i$ from a global bimodal fit giving the exchange rate ($k_i+k_e$) and fraction $X_{i,0}$ (see FIG. 18).

According to another specific embodiment of the present invention, a method is provided wherein an asymmetric pulse pair or gradient modulation is used to increase the filter efficiency. The time integral of the effective gradient modulation should however evaluate to zero at the end of the diffusion weighting block.

According to yet another specific embodiment of the present invention, the pulse time δ is varied at a constant effective diffusion time $t_d$ to achieve a more accurate estimation of the intracellular fraction $X_{i,2}$ ($t_{mix}$) (see FIG. 20).

According to one specific embodiment of the present invention a numerical optimization is made to increase the filter efficiency (see FIG. 15).

Moreover, according to another specific embodiment of the present invention a global fit and/or a constrained ILT (Inverse Laplace Transform) with subsequent fit of intracellular fractions to analyse data is made. As an example FIG. 18 shows the global fit of data obtained according to protocol 3) above in the section of new protocols according to the present invention and FIGS. 19A and B shows the constrained ILT with subsequent fit of intracellular fractions of data obtained according to protocol 3) above in the section of new protocols according to the present invention.

According to specific embodiments there is provided the use of the method according to the specific embodiment of the present invention, as a diagnostic tool for diagnosing a disease or disorder, for studying the metabolism of living cells in vivo or for studying the transmembrane diffusion of a medical drug through the cell membranes.

According to another embodiment of the present invention, there is provided a medical workstation comprising means for performing the method according to the specific embodiment above.

According to yet another embodiment of the present invention there is provided a system for magnetic resonance imaging or nuclear magnetic resonance spectroscopy comprising a radio frequency pulse unit (81) for emitting a radio frequency pulse sequence towards an object being subjected to a magnetic field, wherein said object comprises a molecule having an atom with a nuclear spin differing from 0,
a gradient pulse unit (82) for emitting a gradient pulse sequence towards said object,
a detector unit (83) for detecting a magnetic resonance signal from said object corresponding to said emitted radio frequency pulse sequence,
wherein said gradient pulse sequence comprises a first diffusion weighting block with an amplitude $G_1$, a mixing block with duration $t_{mix}$ and a second diffusion weighting block with an amplitude $G_2$, wherein all of $G_1$, $t_{mix}$ and $G_2$ are either varied, fixed or in on or off mode and at least one of $G_1$ or $G_2$ is fixed or in on or off mode.

Moreover, according to another specific embodiment, the system according to above further comprises an image creation unit (85) configured to create an image based on said magnetic resonance signal.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

The invention claimed is:

1. A method for magnetic resonance imaging or nuclear magnetic resonance (NMR) spectroscopy comprising:

emitting a radio frequency pulse sequence from a radio frequency pulse unit towards an object being subjected to a magnetic field, wherein said object comprises a molecule having an atom with a nuclear spin differing from 0;

emitting a gradient pulse sequence from a gradient pulse unit towards said object;

detecting in a detector unit, and acquiring a magnetic resonance signal from said object corresponding to said emitted radio frequency pulse sequence, wherein said gradient pulse sequence comprises a first diffusion weighting gradient block with an amplitude $G_1$, a mixing block with duration $t_{mix}$ and a second diffusion weighting gradient block with an amplitude $G_2$, wherein all of $G_1$, $t_{mix}$ and $G_2$ are either varied, fixed or in on or off mode, wherein the on or off mode has a variable taking one of two values where a first value is zero and a second value is finite, and at least one of $G_1$ or $G_2$ is fixed or in on or off mode; and wherein an integral of a gradient over time equals zero within each of the first diffusion weighting gradient block and the second diffusion weighting gradient block.

2. The method according to claim 1, wherein one of the following is valid:

$G_1$ is in on or off mode, $G_2$ is fixed and $t_{mix}$ is fixed;

$G_2$ is in on or off mode, $G_1$ is fixed and $t_{mix}$ is fixed;

$G_1$ is in on or off mode, $G_2$ is fixed and $t_{mix}$ is varied;

$G_2$ is in on or off mode, $G_1$ is fixed and $t_{mix}$ is varied;

$G_1$ is fixed, $G_2$ is varied and $t_{mix}$ is varied, which is complemented by a series where $G_1$ equals zero, $t_{mix}$ is fixed and $G_2$ is varied; or $G_2$ is fixed, $G_1$ is varied and $t_{mix}$ is varied, which is complemented by a series where $G_2$ equals zero, $t_{mix}$ is fixed and $G_1$ is varied.

3. The method according to claim 1, further comprising using an asymmetric pulse pair or gradient modulation to increase filter efficiency.

4. The method according to claim 1, further comprising varying a pulse time at a constant effective diffusion time, $t_d$.

5. The method according to claim 1, further comprising making a numerical optimization to increase filter efficiency.

6. The method according to claim 1, further comprising performing either or both of a global fit and a constrained ILT (Inverse Laplace Transform) of the NMR signal, with subsequent fit of intracellular fractions to analyze data.

7. The method according to claim 1, wherein further comprising creating an image in an digital image creation unit, based on the magnetic resonance signal.

* * * * *